United States Patent
Chang et al.

(10) Patent No.: US 9,925,308 B2
(45) Date of Patent: Mar. 27, 2018

(54) INJECTABLE COMPOSITION FOR IN-SITU REPAIR AND REGENERATION OF AN INJURED LIGAMENT OR TENDON AND METHODS OF USE

(71) Applicant: The Board of Trustees of the Leland Stanford Junior University, Palo Alto, CA (US)

(72) Inventors: James Chang, Stanford, CA (US); Hung Pham, Milpitas, CA (US); Colin Woon, Chicago, IL (US); Simon Farnebo, Palo Alto, CA (US); Anais Legrand, Palo Alto, CA (US)

(73) Assignees: THE BOARD OF TRUSTEES OF THE LELAND STANFORD JUNIOR UNIVERSITY, Stanford, CA (US); THE UNITED STATES OF AMERICA AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 14/855,034

(22) Filed: Sep. 15, 2015

(65) Prior Publication Data
US 2016/0166735 A1 Jun. 16, 2016

Related U.S. Application Data

(63) Continuation-in-part of application No. PCT/US2014/028525, filed on Mar. 14, 2014.

(60) Provisional application No. 61/789,336, filed on Mar. 15, 2013.

(51) Int. Cl.
| | |
|---|---|
| A61L 27/36 | (2006.01) |
| A61L 27/38 | (2006.01) |
| A61L 27/58 | (2006.01) |
| A61L 27/52 | (2006.01) |
| A61L 27/24 | (2006.01) |
| A61L 27/54 | (2006.01) |
| A61K 38/28 | (2006.01) |
| A61K 35/12 | (2015.01) |
| A61K 45/06 | (2006.01) |
| A61K 35/16 | (2015.01) |
| A61L 27/50 | (2006.01) |

(52) U.S. Cl.
CPC .............. *A61L 27/52* (2013.01); *A61K 35/12* (2013.01); *A61K 35/16* (2013.01); *A61K 38/28* (2013.01); *A61K 45/06* (2013.01); *A61L 27/24* (2013.01); *A61L 27/3633* (2013.01); *A61L 27/3662* (2013.01); *A61L 27/3687* (2013.01); *A61L 27/3804* (2013.01); *A61L 27/386* (2013.01); *A61L 27/3834* (2013.01); *A61L 27/50* (2013.01); *A61L 27/54* (2013.01); *A61L 27/58* (2013.01); *A61L 2300/252* (2013.01); *A61L 2300/402* (2013.01); *A61L 2300/406* (2013.01); *A61L 2300/412* (2013.01); *A61L 2300/414* (2013.01); *A61L 2300/45* (2013.01); *A61L 2300/64* (2013.01); *A61L 2400/06* (2013.01); *A61L 2430/10* (2013.01); *A61L 2430/40* (2013.01)

(58) Field of Classification Search
None
See application file for complete search history.

(56) References Cited

U.S. PATENT DOCUMENTS

| | | | | |
|---|---|---|---|---|
| 2009/0253810 | A1* | 10/2009 | Katz | ...................... A61K 35/32 514/773 |
| 2012/0114755 | A1 | 5/2012 | Amadio et al. | |
| 2012/0264190 | A1 | 10/2012 | Christman et al. | |

FOREIGN PATENT DOCUMENTS

WO WO2010101883 A2 9/2010

OTHER PUBLICATIONS

Wallace, Donald G; Rosenblatt, Joel; "Collagen gel systems for sustained delivery and tissue engineering" Advanced Drug Delivery Review, 55, 1631-1649, 2003.*
Silver, Frederick H; et al; "Collagen self-assembly and the development of tendon mechanical properties" Journal of Biomechanics, 36, 1529-1553, 2003.*
Chang James: "Studies in Flexor Tendon Reconstruction: Biomolecular Modulation of Tendon Repair and Tissue Engineering," The Journal of Hand Surgery, vol. 37, No. 3, Mar. 2012, pp. 552-561.
Gundula Schulze-Tanzil et al.: "Decellularized Tendon Extracellular Matrix—A Valuable Approach For Tendon Reconstruction?", Cells, vol. 4, No. 1, Nov. 5, 2012, pp. 1010-1012.

* cited by examiner

*Primary Examiner* — David W Berke-Schlessel
(74) *Attorney, Agent, or Firm* — Stanford University; Andrea Blecken

(57) ABSTRACT

The invention provides an injectable composition and method for the minimally invasive, in-situ repair and regeneration of an injured ligament or tendon in a mammalian subject. The composition is also useful for the delivery of growth factors, therapeutic agents and cells into the area of tendon or ligament injury.

17 Claims, 34 Drawing Sheets

UNDER(-)  RIGHT (+)  OVER(-)

Top

Bottom 7 day explant  14 day explant  28 day explant
0.48g           0.47g            0.32g

Fig. 14

| Protein | Percentage |
|---|---|
| Collagen (total) | 32.3% |
| COL6A3 | 17.1% |
| COL6A2 | 9.2% |
| COL1A2 | 2.0% |
| COL14A1 | 1.3% |
| COL6A1 | 0.3% |
| COL1A1 | < 0.1% |
| COL5A2 | < 0.1% |
| COL3A1 | < 0.1% |
| Tenascin X-like | 8.3% |
| Vimentin-like | 3.7% |
| Decorin | 3.4% |
| Fibromodulin-like | 3.0% |
| Albumin | 2.9% |
| Biglycan | 2.4% |
| CILP 2 | 2.1% |
| Beta-actin | 2.1% |
| Annexin | 2.0% |
| Prolargin-like | 1.6% |
| Mimecan-like | 1.6% |
| COMP | 1.5% |
| Keratocan-like | 1.4% |
| Fibrillin-1 | 1.3% |
| Other | 29.4% |

Fig. 15, continued
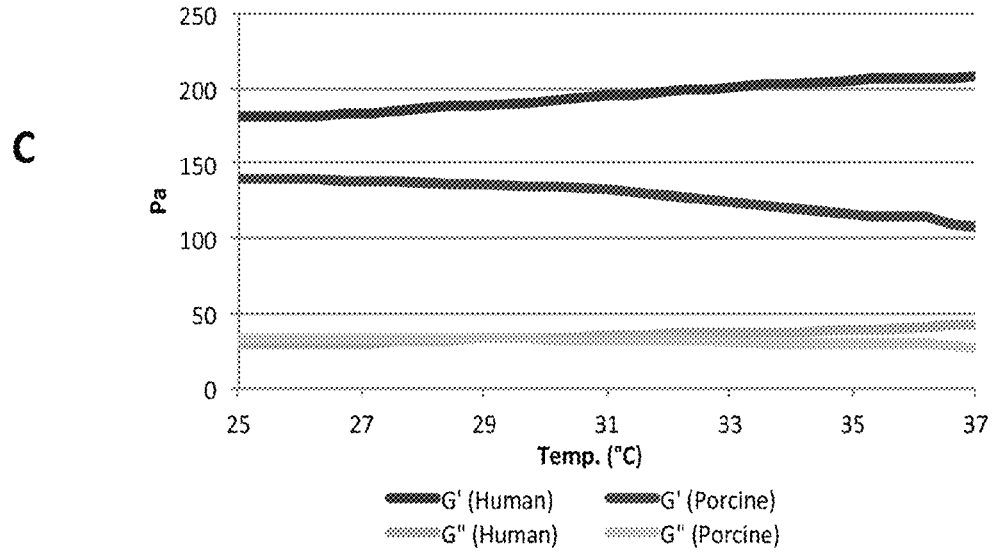
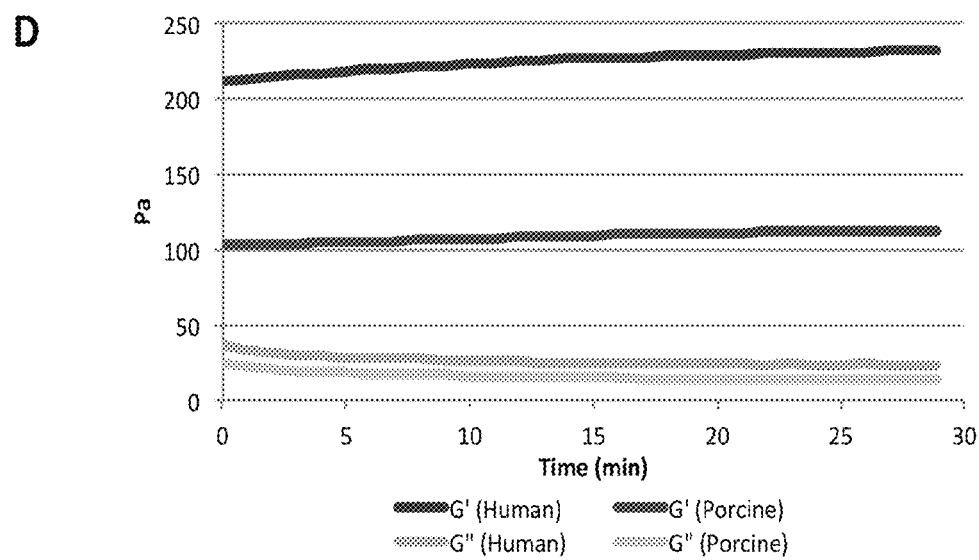

left          right left          right

C=calcaneus, G=gastrocnemius muscle, A=Achilles tendon

INJECTABLE COMPOSITION FOR IN-SITU REPAIR AND REGENERATION OF AN INJURED LIGAMENT OR TENDON AND METHODS OF USE

1. CROSS-REFERENCE TO RELATED APPLICATION

This application is a continuation-in-part application of International Application PCT/US14/28525, with an international filing date of Mar. 14, 2014, that is entitled "Injectable Composition For In-Situ Repair and Regeneration of An Injured Ligament Or Tendon And Methods of Use" and claims priority and other benefits from U.S. Provisional Patent Application Ser. No. 61/789,336 filed Mar. 15, 2013, entitled "Injectable tendon hydrogel as a scaffold for in-situ guided tendon and ligament repair and regeneration and methods of use". Its entire content is specifically incorporated herein by reference.

2. TECHNICAL FIELD OF THE INVENTION

The invention relates generally to the treatment of ligament and tendon injuries. Particularly, the invention provides an injectable tendon-derived composition for the minimally invasive, in-situ repair of ligament and tendon injuries such as tears that result acutely from trauma or chronically from tendon or ligament overuse. The tendon-derived composition is applied in solubilized form and polymerizes upon administration to the defect of an injured ligament or tendon, where it fills out and conforms to the defect, thereby creating a scaffold which attracts and guides the recruitment of new tenoblasts, tenocytes and fibroblasts inside the defect for repair and regeneration of the injured ligament or tendon.

3. BACKGROUND

Tendons and ligaments are strong bands of fibrous connective tissue that consist to a great part of collagen fibers. While tendons connect muscle to bone, ligaments connect bone to bone across a joint. The point of connection between muscle and tendon is the myotendinous junction or also called tendon-muscle insertion, and the point of connection between tendon and bone is the osteotendinous junction. The osteotendinous junction, where collagen fibrils from the tendon insert into the bone matrix, is a site of frequently occurring tendinopathies that are commonly caused by tendon overuse. Tendon overuse leads to significant histological and biochemical changes that alter the biomechanical and material properties in tendons and ligaments (Arya & Kulig, 2010), causing accumulative microscopic tears that ultimately result in complete tears. Tears may be graded as minimal (1st degree), moderate to severe (2nd degree), or complete (3rd degree). Such injuries are most commonly seen in the rotator cuff, Achilles tendon, quadriceps tendon, and patella tendon as well as in medial and lateral epicondylitis of the elbow.

Some ligaments limit the mobility of a joint or prevent certain movements altogether. Ligaments are elastic and lengthen under tension, unlike tendons, which are inelastic.

Sports medicine specialists are frequently faced with the need to repair and regenerate ligaments and tendons that are injured in ways that result in tears during everyday activities involving high-impact repetitive movements such as running, playing soccer or golf. Readily available materials for quick and efficient, minimally invasive administration and treatment are, therefore, needed. The methods and compositions of the present invention address this need.

4. SUMMARY OF THE INVENTION

In one aspect, the present invention provides a composition comprising decellularized extracellular matrix derived from tendon connective tissue for in-situ repair and regeneration of an injured ligament or tendon in a mammalian subject. The composition is in an injectable form below 25 degree Celsius and polymerizes to a hydrogel upon administration into the subject's area of injured ligament or tendon where it is effective in repairing and regenerating said injured ligament or tendon. In certain embodiments, the resulting hydrogel forms in situ a support structure which facilitates infiltration of the subject's own fibroblasts, tenoblasts and tenocytes into said support structure and, thereby, facilitates in-situ repair and regeneration of injured ligament or tendon. In some embodiments, a one-time administration of the hydrogel is sufficient for treatment, in other embodiments repeated administration may be needed.

In certain embodiments, the tendon connective tissue is selected from a human donor; in other embodiments, the tendon connective tissue is selected from an animal donor such as a pig.

In some embodiments, the composition creates, upon gelation, a structure suitable for infiltration of host cells such as fibroblasts, tenoblasts and tenocytes. In other embodiments, cells such as stem cells, progenitor cells or fibroblasts, and/or therapeutic agents such as growth factors and/or platelet-rich plasma can be added to the composition prior to administration to increase its in-situ therapeutic benefit for tendon or ligament repair and regeneration. In other embodiments, the therapeutic agent is a small molecule or protein exhibiting antibacterial effects or analgesic effects in order to ameliorate pain or a risk of infection that may occur concomitant with the tendon or ligament injury.

In a further aspect, the invention provides a method for in-situ repair and regeneration of an injured tendon or ligament in a mammalian subject, which involves the administration of a composition comprising decellularized extracellular matrix derived from tendon connective tissue to the area of injured tendon or ligament. The composition is in an injectable form below 25 degree Celsius and polymerizes to a hydrogel upon administration into the subject's area of injured ligament or tendon where it is effective in repairing and regenerating said injured ligament or tendon. In certain embodiments, the resulting hydrogel forms in situ a support structure which facilitates infiltration of the subject's own fibroblasts, tenoblasts and tenocytes into said support structure and, thereby, facilitates in-situ repair and regeneration of injured ligament or tendon. In some embodiments, a one-time administration of the hydrogel is sufficient for treatment, in other embodiments repeated administration may be needed.

In another aspect, the invention provides a method of producing a composition comprising decellularized extracellular matrix derived from tendon connective tissue for in-situ repair and regeneration of an injured ligament or tendon in a mammalian subject. In some embodiments, the tendon extracellular matrix is derived from an allogeneic source such as a human. In other embodiments, the tendon extracellular matrix is derived from a xenogeneic source such as a pig.

The above summary is not intended to include all features and aspects of the present invention nor does it imply that the invention must include all features and aspects discussed in this summary.

5. INCORPORATION BY REFERENCE

All publications mentioned in this specification are herein incorporated by reference to the same extent as if each individual publication was specifically and individually indicated to be incorporated by reference.

6. BRIEF DESCRIPTION OF THE DRAWINGS

The accompanying drawings illustrate embodiments of the invention and, together with the description, serve to explain the invention. These drawings are offered by way of illustration and not by way of limitation; it is emphasized that the various features of the drawings may not be to-scale.

FIG. 1 illustrates, as detailed in Example 1, the determination of successful digestion of the tendon extracellular matrix (ECM) solution as a function of time, pH during the digestion and concentration of tendon powder (see also Table 1). The digestion of the ECM solution was observed at 20× magnification every 12 h. The degree of digestion was recorded as underdigested "UNDER (−)", adequate "RIGHT (+)", and overdigested "OVER (−)" based on homogeneity (adequate), degree of remaining tendon flakes (underdigested) and single collagen fibers (adequate). This estimation corresponded well to gelation of the ECM solution at 37° C., (−) no gelation, (+/−) weak gelation, (+) gelation. In conclusion, optimal digestion is needed in order to obtain favorable gelation characteristics and the desired thermosensitivity of the ECM solution, which makes possible the administration of the tendon extracellular matrix in solubilized form at a temperature that is considerably lower than body temperature (assuming 37° Celsius as physiological or body temperature), preferably at 4° Celsius and within a range of 4-25° Celsius, followed, upon administration into a defect, by gelation at body temperature.

Figure 4A:
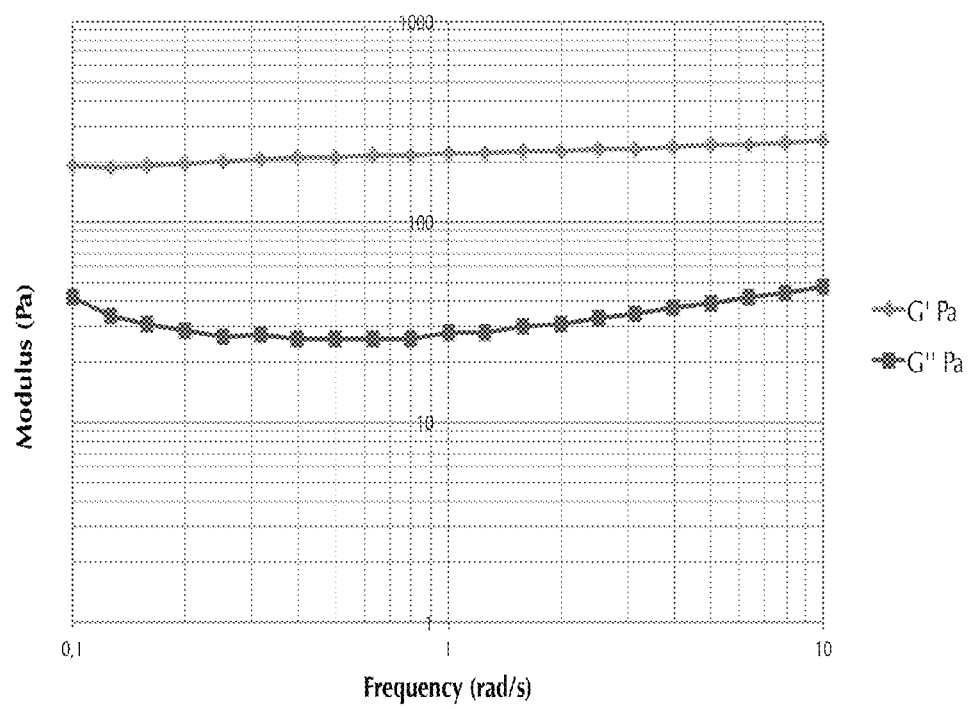
FIG. 4A illustrates the measurement of rheological data from one representative sample of tendon hydrogel, as further described in Example 1, as a measurement of its mechanical properties; triplicates of the storage (G') and loss (G") moduli for the tendon hydrogel are shown: G' at 1 rad/s is 217 and G" is 28 in this sample (average G' is 213.1 and G" 27.1).
Figure 4B:
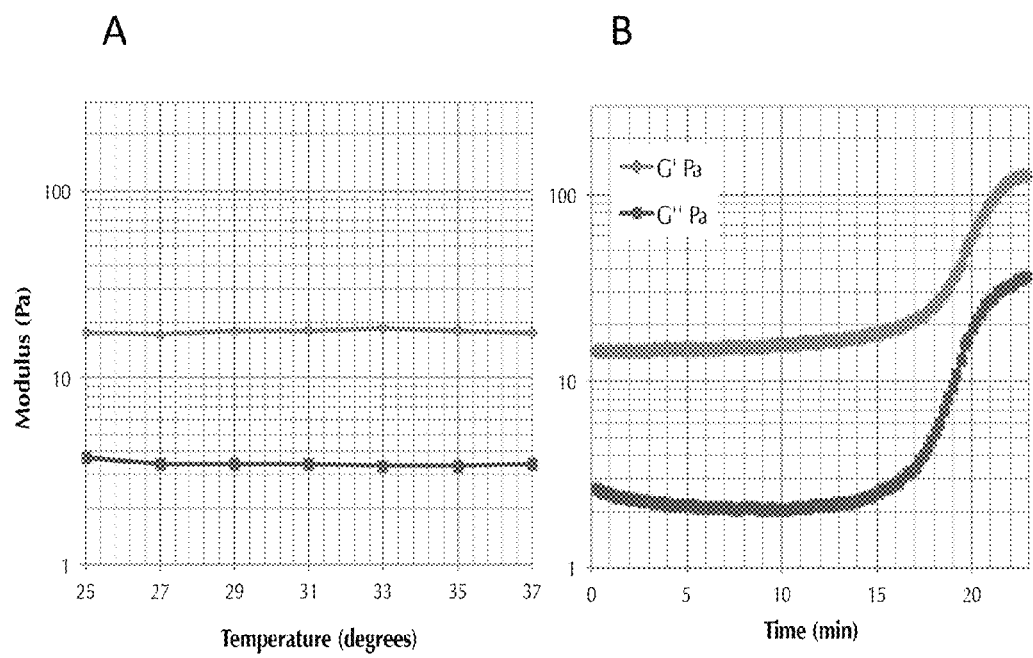

FIG. 4B shows a kinetic determination of hydrogel formation (in triplicates) as a function of temperature, as further described in Example 1. In panel A, the temperature was slowly increased from 25 to 37° C., with a 2° C. increase per minute. Note that the moduli of the solution remained low (i.e. weak) and did not change during this time. In panel B, the temperature was kept constant at 37° C., and the tendon ECM solution was allowed to gelate without further increases in temperature. Both the storage modulus (G') and the loss modulus (G") increased as a function of time, depicted as a sigmoidal shaped increase. This process was initiated approximately after 15 minutes at 37° C., with a plateau that was reached after 20 minutes. Thus, solubilized tendon extracellular matrix remained liquid at temperatures below 37° C., however, it started to change its viscoelastic properties from 37° Celsius on, at which point it polymerized into a gel. This change occurs at approximately 20 minutes, which also corresponds to the time it takes for the tendon ECM solution to completely form a gel in vitro, as observed macroscopically.

Figure 5:
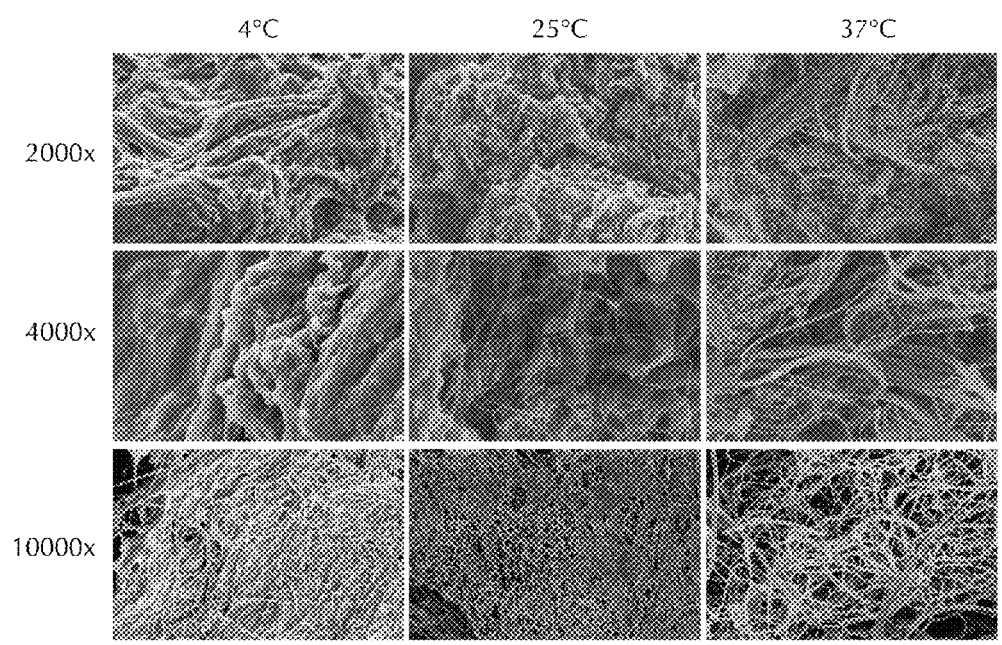

In FIG. 5, scanning electron microscope (SEM) images of in-vitro polymerization of the tendon hydrogel illustrate that improved fiber definition correlated with increased temperature, and nanoscale collagen features at 37° C., as described in Example 1.

Figure 6:
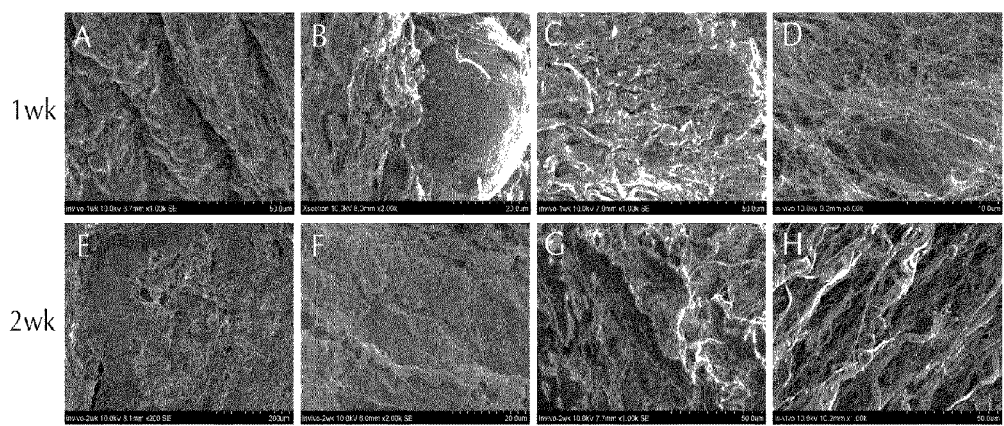

FIG. 6 illustrates scanning electron microscope images of gels with cells, harvested 1 (1 wk) and 2 (2 wk) weeks after in vivo application, as further explained in Example 1. Collagen fibrils often have a linear arrangement with collagen defined as a porous network or linear bundles interspaced with cavities (2 wk, H). Collagen bundles are highly regular with a clear longitudinal orientation along the underlying muscular surface (shown in 1 wk, A). Cells follow this linear arrangement in surface view (1 wk, C and 2 wk, F). Cells are closely adherent to fibers (B), and there is an apparent integration of the gel patch with the surrounding tissue (2 wk, E). Cells grow invasively into the collagen scaffold (1 wk, D; 2 wk, G) and become increasingly aligned and confluent, and integrated with the gel scaffold.

Figure 7:
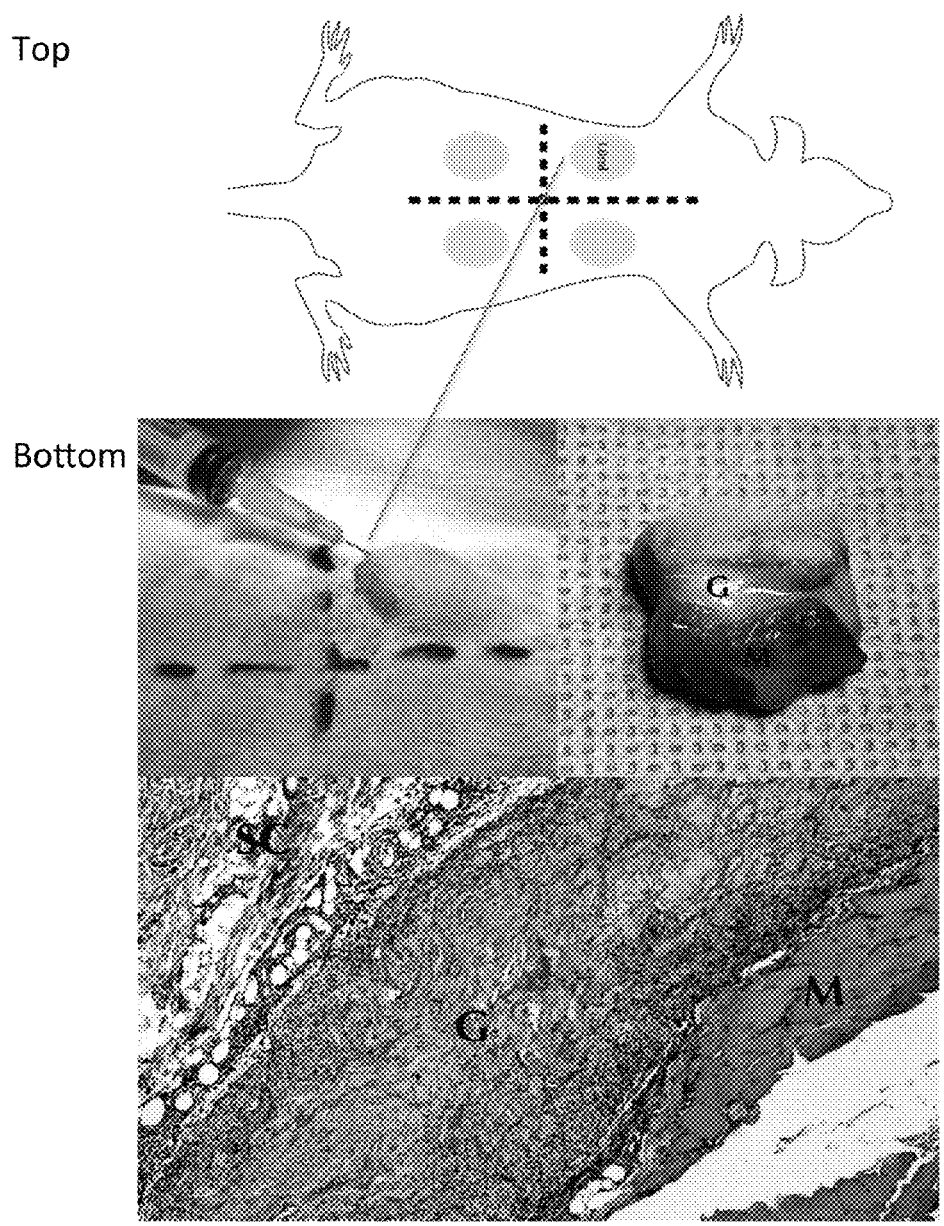

FIG. 7 illustrates, as further explained in Example 1, the percutaneous administration of tendon extracellular matrix solution (1 ml per injection site, 4 sites per 350 g rat) into the back of immune-competent Wistar rats and subsequent tendon hydrogel (G) formation in the subcutaneous space that surrounded the site of administration. The top panel indicates where in the rats the extracellular matrix solution was injected. The gel was consistently confined to the subcutaneous space beneath the panniculus carnosus, subcutaneous fat (SC) and underlying para-spinal muscle (M). Hematoxylin and eosin (H&E) histological analysis (with a magnification of 20×), bottom, shows the gel (G) with vast cellular ingrowth from surrounding tissues already at 3 days post injection.

Figure 8:
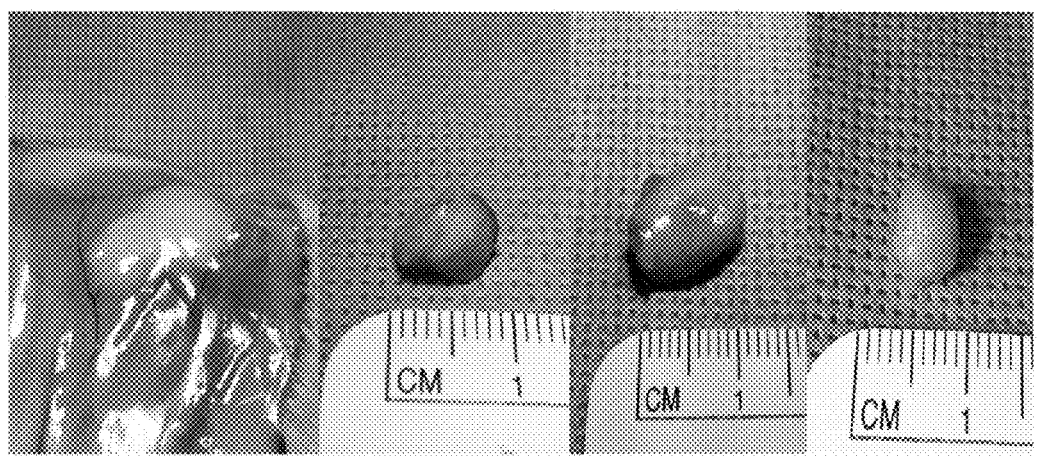

FIG. 8 illustrates, on the very left, the position and size of an exemplary tendon-derived hydrogel 7 days following percutaneous injection into the back of a Wistar rat, as further explained in Example 1. The other panels show representative examples of tendon-derived hydrogel explants that were isolated from Wistar rats at 7, 14 and 28 days after percutaneous injection. The explants are shown with skin, panniculus carnosus, and subcutaneous fat removed.

Figure 9:
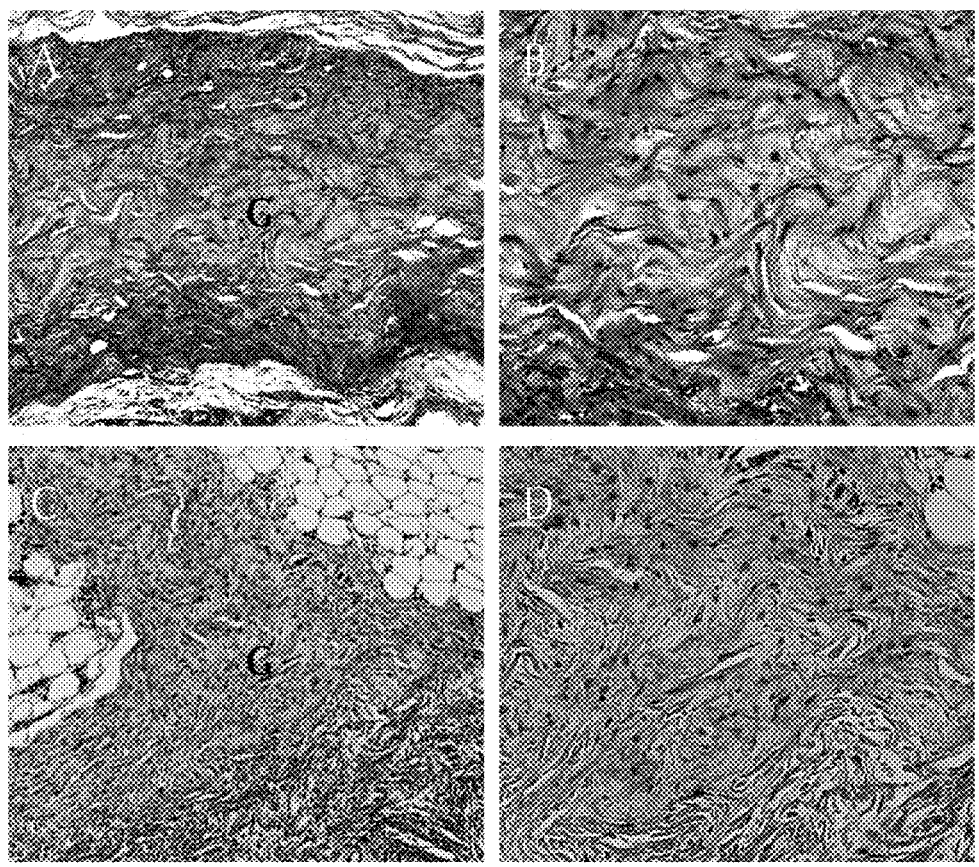

FIG. 9 shows, as further explained in Example 1, the results from Hematoxylin and eosin (H&E) histological analysis of exemplary tendon-derived hydrogels at 2 and 4 weeks following injection into Wistar rats; panel A shows at 20× magnification after two weeks and panel B at 40× magnification after two weeks. The invasion of cells from surrounding tissues into the superficial aspects of the gel as well as the longitudinally aligned fibroblast cells in the centre are notable. Panel C shows at 20× magnification after four weeks and panel D at 40× magnification after four weeks. Note that, at four weeks, the elongated fibroblasts are more homogenously distributed throughout the tendon-derived hydrogel. No signs of capsule formation are present around the gel, indicating integration with surrounding connective tissue.

Figure 10:
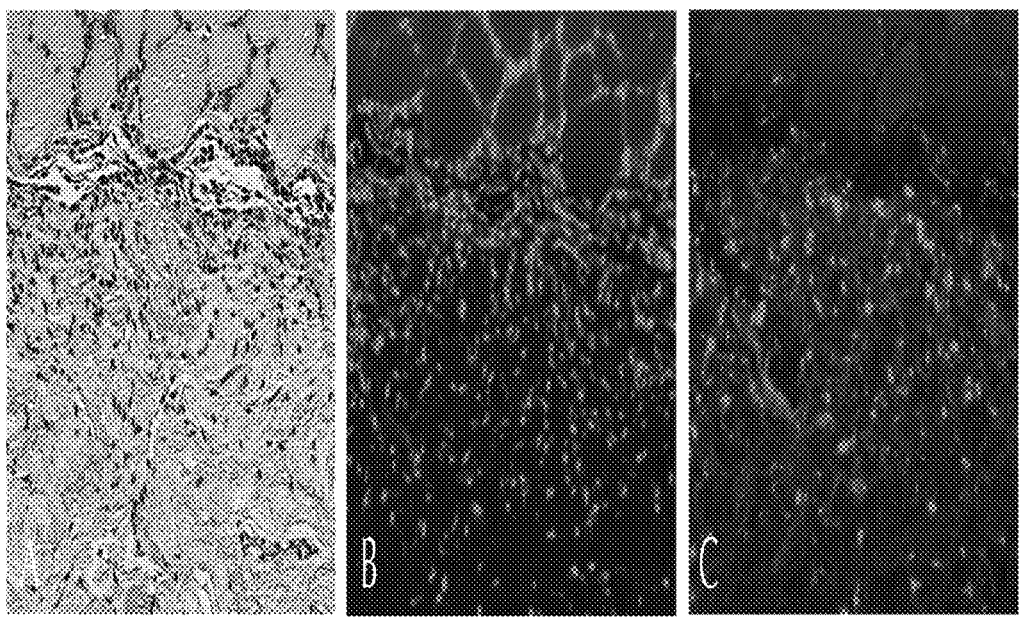

FIG. 10 shows, as further explained in Example 1, results from various staining experiments with tendon-derived hydrogel three days following percutaneous administration into Wistar rats. (A) H&E staining of superficial aspects of tendon-derived hydrogel and para-spinus muscle. Corresponding counterstain of adjacent sections with PI (B) and IHC of CD68+ cells (C) showing invasion of CD 68+ macrophages into the gel (all 20×).

Figure 11:
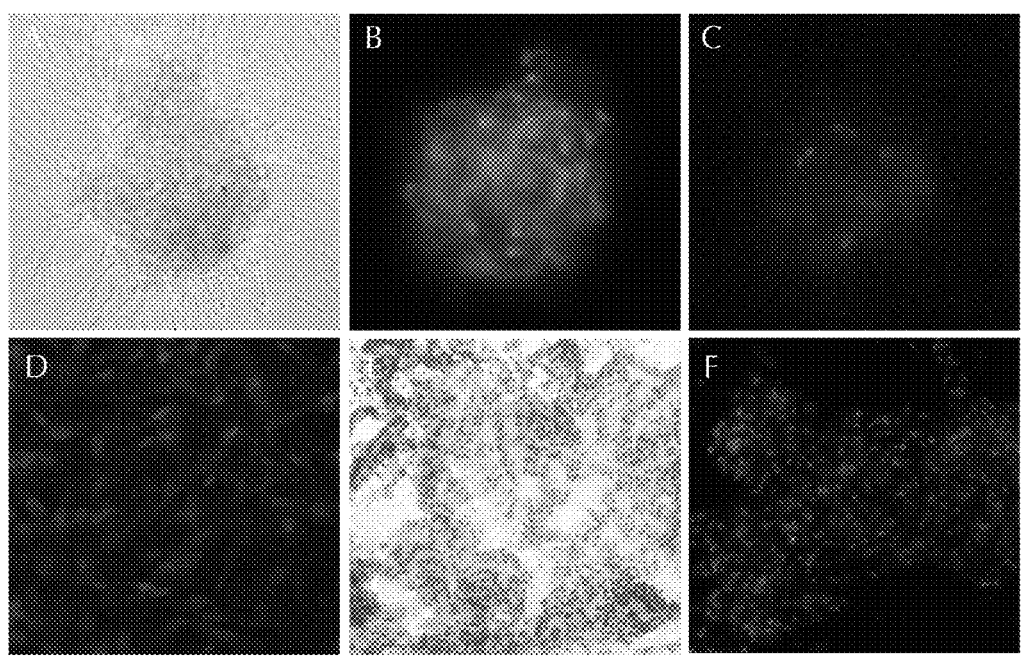

FIG. 11, as further explained in Example 1, shows exemplary tendon-derived hydrogels, where the tendon extracellular matrix solution was seeded with multipotent adipo-derived stem cells (ASCs) prior to gelation. The cells proliferated on the surface and infiltrated the gel, as detailed in panels A-F (with 20× magnification). Panel A shows polymerized gel with cells in culture 5 days post reseeding; live/dead stain of the same piece of gel; panel B shows the live cells in green and panel C shows dead cells in red. Panel D shows SYTO green stain of cells on gel surface, panel E H&E histological analysis of cryosection and panel F corresponding SYTO green analysis.

Figure 12A:
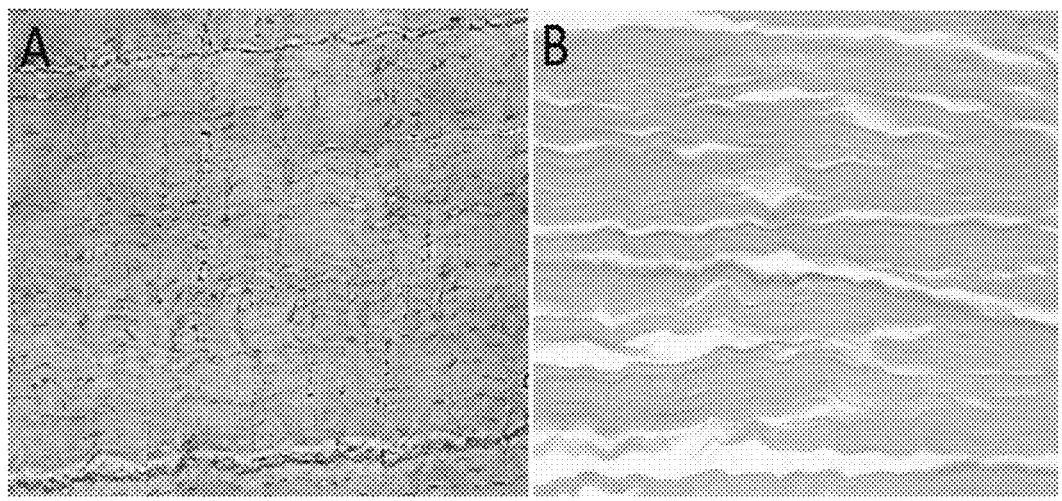
Figure 12B:
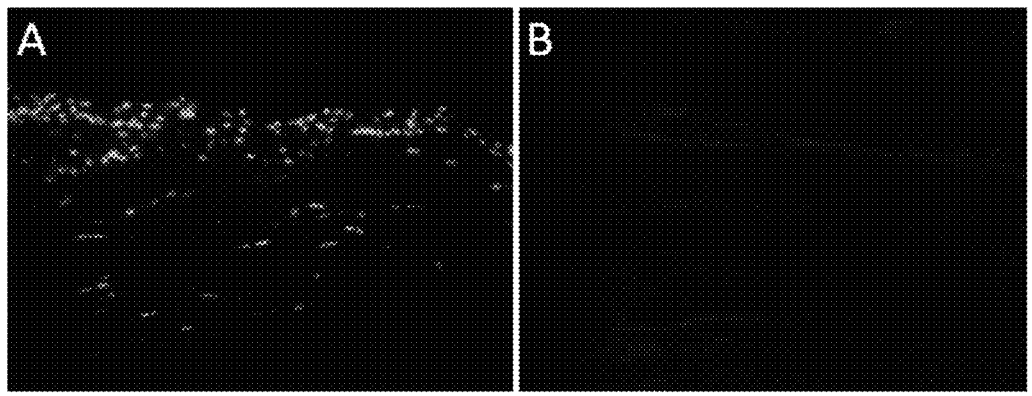

FIGS. 12A and 12B shows results from decellularizing porcine tendon tissue, as further detailed in Example 2. FIG. 12A: H&E staining of native (A) and treated (B) porcine tendon at 20× magnification. In contrast to the native tendon, no cells can be observed between fibrous connective tissue. FIG. 12B: SytoGreen 11 fluorescent staining of native (A) and treated (B) porcine tendon at 20× magnification. Decellularization is confirmed by the absence of fluorescent nuclei in the treated specimen.

Figure 13:
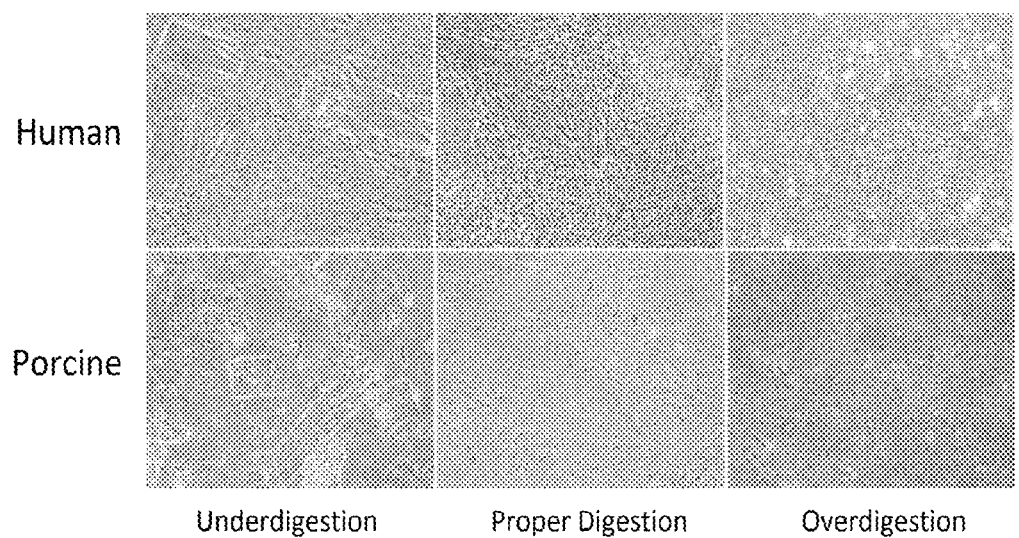

FIG. 13 illustrates, as detailed in Example 2, the determination of successful digestion of porcine tendon extracellular matrix (Porcine) versus human tendon extracellular matrix (Human) based on homogeneity, degree of remaining tendon flakes and single collagen fibers. The degree of digestion was recorded as underdigestion, proper digestion or overdigestion.

FIG. 14 illustrates the approximate protein composition of porcine tendon powder. Collagen IV and Collagen I were the predominant proteins found in the sample. Other peptides included tenascin, vimentin, fibromodulin, decorin, and other extracellular proteins.

Figure 15:
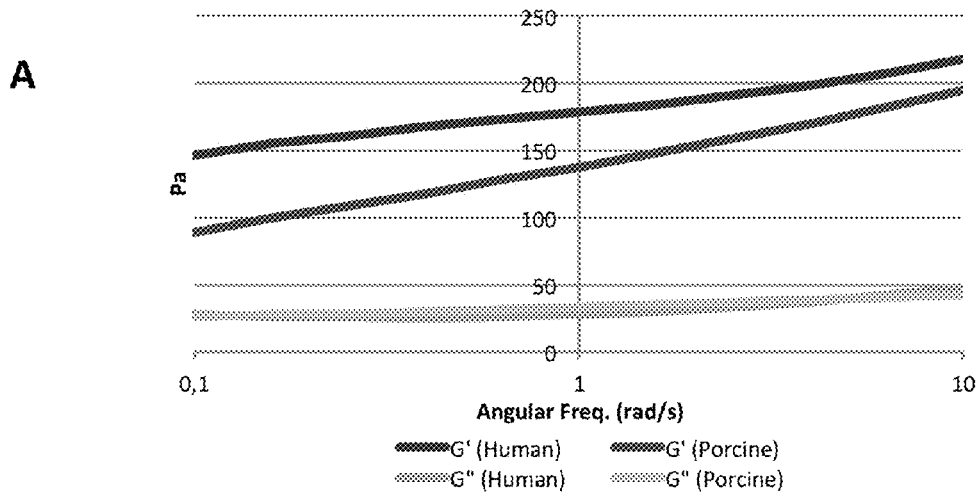
Figure 15:
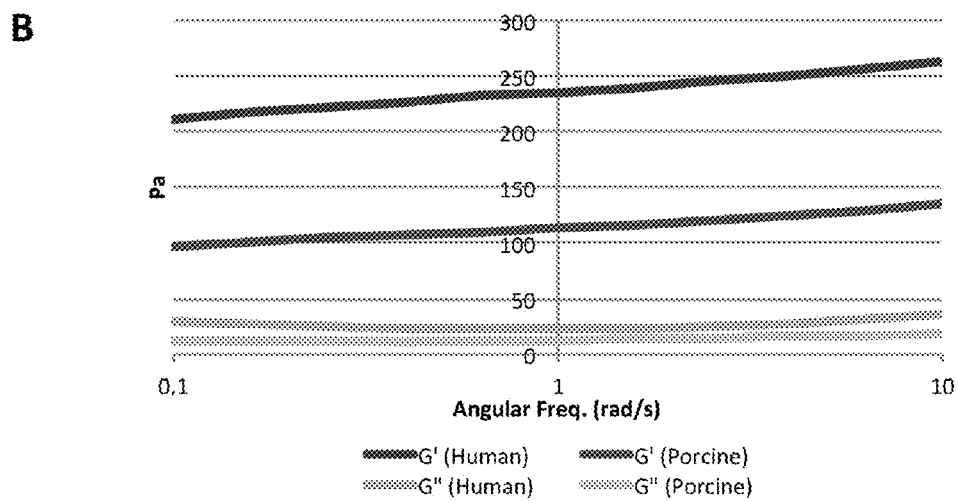

FIG. 15 illustrates the rheological properties of 2% human and 1% porcine tendon-derived extracellular matrix solutions as indicated by the storage (G') and the loss (G") moduli representing the elastic and viscous properties, respectively. Panel A shows frequency sweeps, i.e. testing of the elastic and viscous properties at different oscillation frequencies, of human and porcine tendon-derived matrix at 25° C. Panel B shows frequency sweeps of human and porcine tendon-derived matrix at 37° C. Panel C shows temperature sweeps of human and porcine tendon-derived matrix, where the elastic and viscous properties were tested at different temperatures. Panel D shows time sweeps of human and porcine tendon-derived matrix at 37° C., where the elastic and viscous properties were tested over time.

Figure 16:
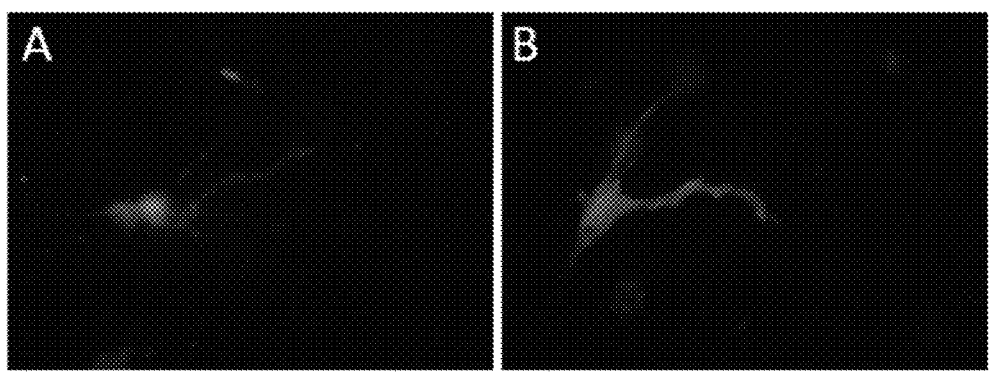

FIG. 16 shows the morphology of human adipo-derived stem cells seeded within 2% human (A) and 1% porcine (B) tendon extracellular matrix solutions. Spindle-shaped cells can be seen throughout each extracellular matrix solution.

Figure 17:
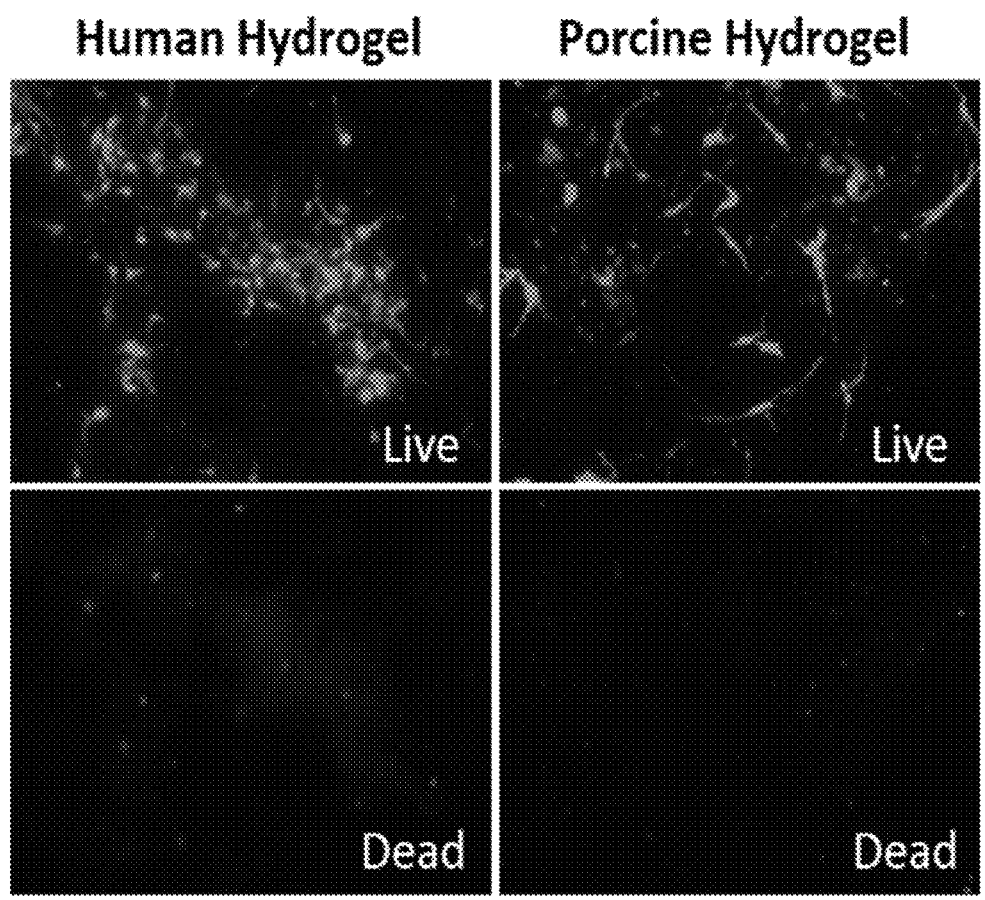

FIG. 17 shows results from the Live/Dead Assay, as further detailed in Example 2. The ratio of viable to non-viable cells remained low for human adipo-derived stem cells within human and porcine tendon-derived hydrogels. Viable cells are seen as green and non-viable cells are seen as red.

Figure 18:
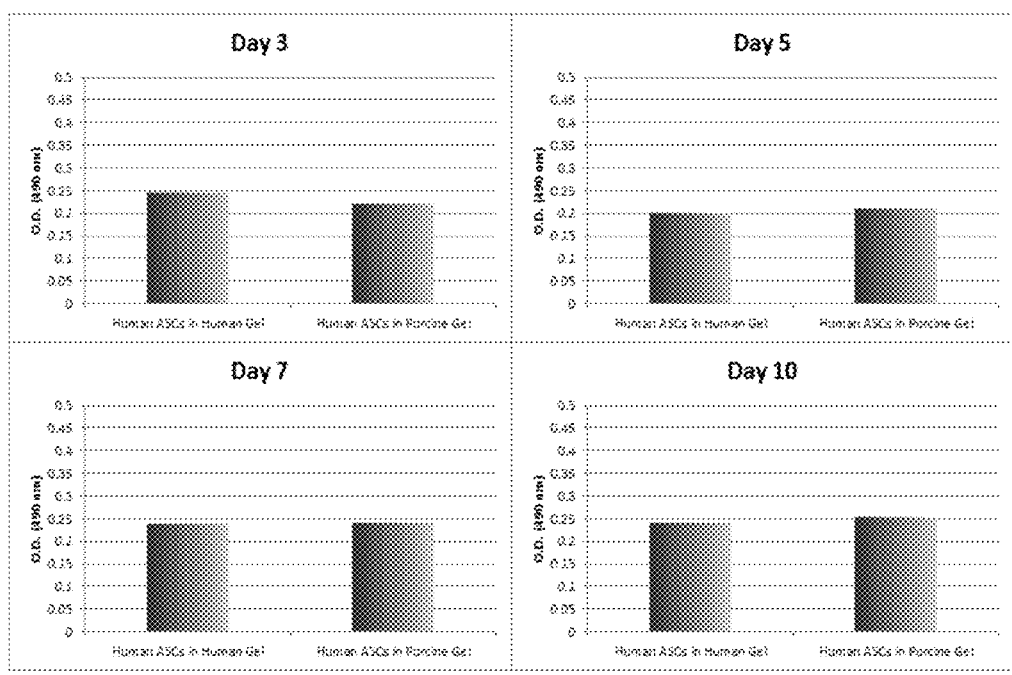

FIG. 18 illustrates the proliferation of human adipo-derived stem cells in human and porcine hydrogel at 3, 5, 7, and 10 days. No difference in proliferation exists at any time point.

Figure 19:
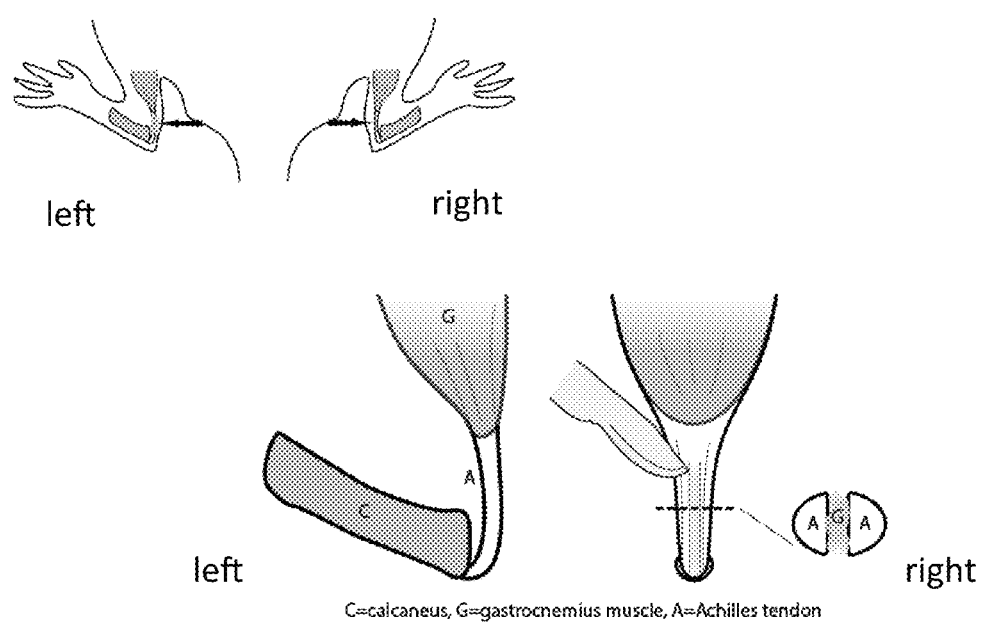

FIG. 19 illustrates the set up of the studies, as detailed in Example 3, where Achilles tendon defects were created in Wistar rats by removing 50% of the Achilles tendon substance in each leg. The resulting defects were filled: on the left side with 2% solubilized tendon-derived extracellular matrix that gelated once administered by injection into the defect at body temperature (37° C.) and filled out the gap that was created by the removal of 50% tendon substance that had produced the defect; on the right side, the defect was filled with saline as control.

Figure 20:
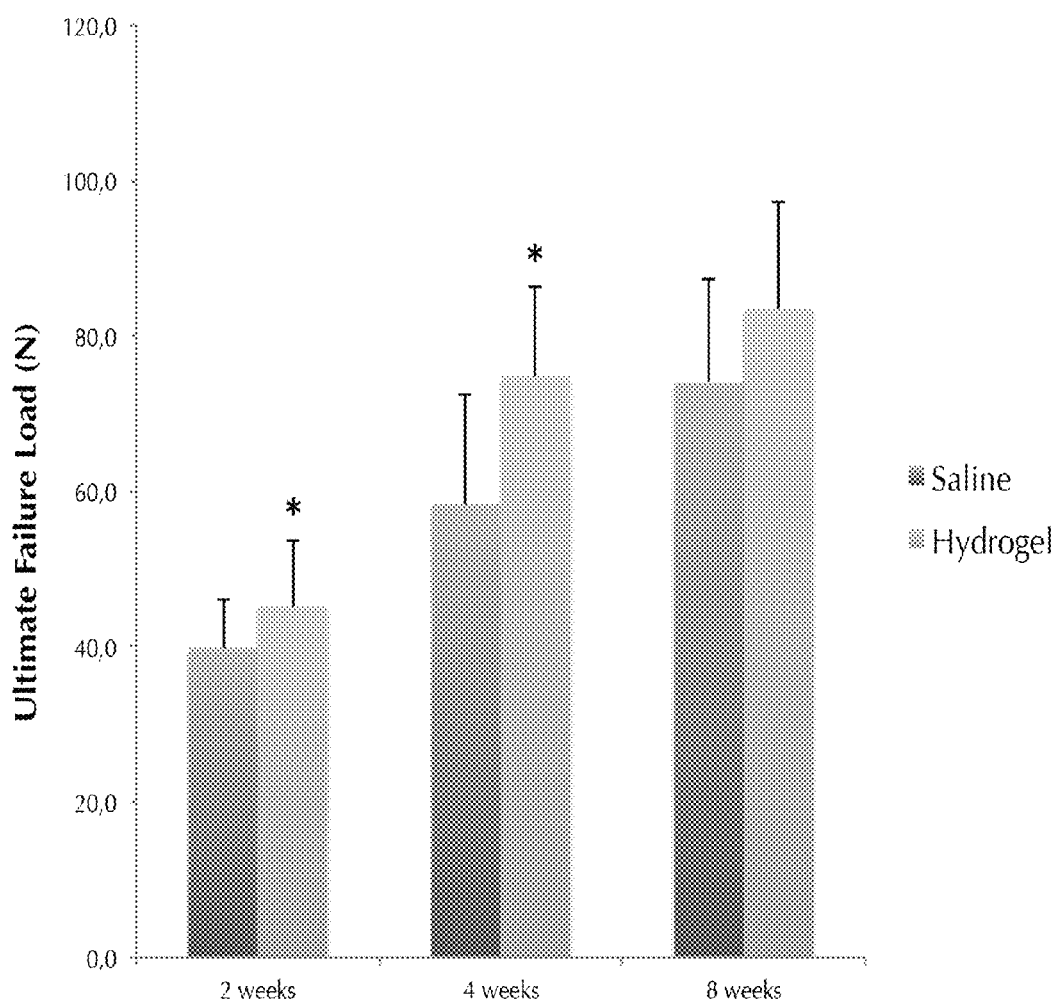

FIG. 20 shows the results of the study described in FIG. 19 and Example 3, where the biomechanical properties of rats' Achilles tendon that was treated with solubilized tendon-derived extracellular matrix that gelated in-situ are compared to rats' Achilles tendon whose defect was treated with saline as control.

Figure 21:
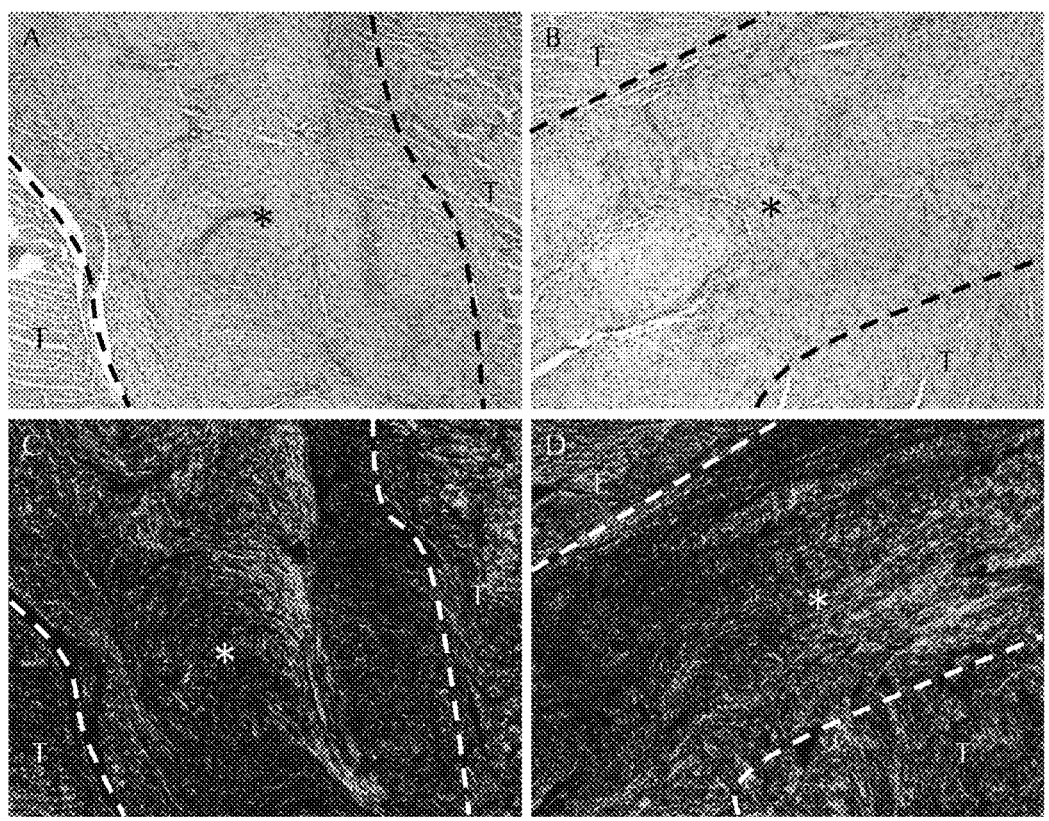

FIG. 21 shows results from H&E staining after 4 weeks of saline versus tendon hydrogel treatment. H&E sections of saline (A) and gel (B) treatment at 4 weeks show typical wound trough morphologies and population by host cells in both groups. Corresponding Picro-sirius Red stains (C/saline & D/gel) show a difference in collagen content between the treatment groups. Whereas the wound troughs of the saline-treated tendons primarily contain collagen III, the wound troughs of the gel-treated tendons show higher concentrations of collagen I. T=tendon, *=wound trough.

Figure 22:
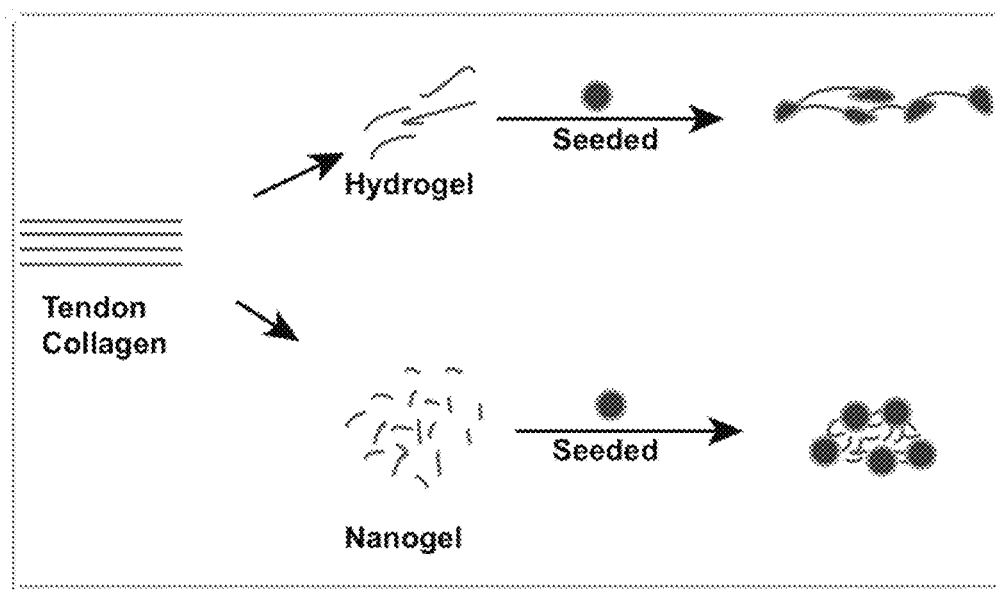

FIG. 22 shows the formation of a nano-matrix scaffold of cells and nanogel (bottom right) upon gelation of seeded tendon extracellular matrix solution that contained nanoscaled fibers that had nano-meter sized collagen fiber diameters, as produced following high frequency ultrasonication.

Figure 23:
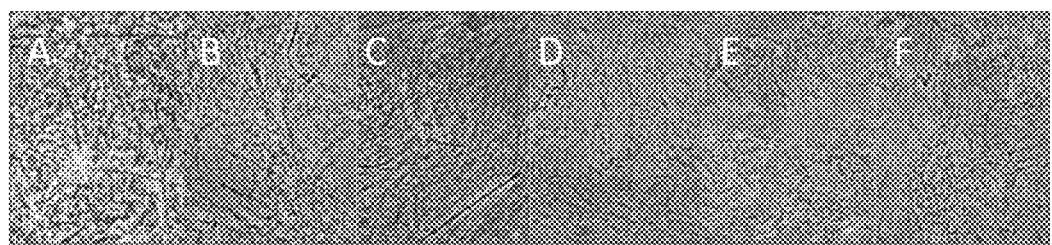

FIG. 23 shows optical microscope pictures of gel samples at 40× magnification. A: Control, B: 2 cycles, C: 10 cycles, D: 20 cycles, E: 40 cycles, F: 60 cycles.

Figure 24:
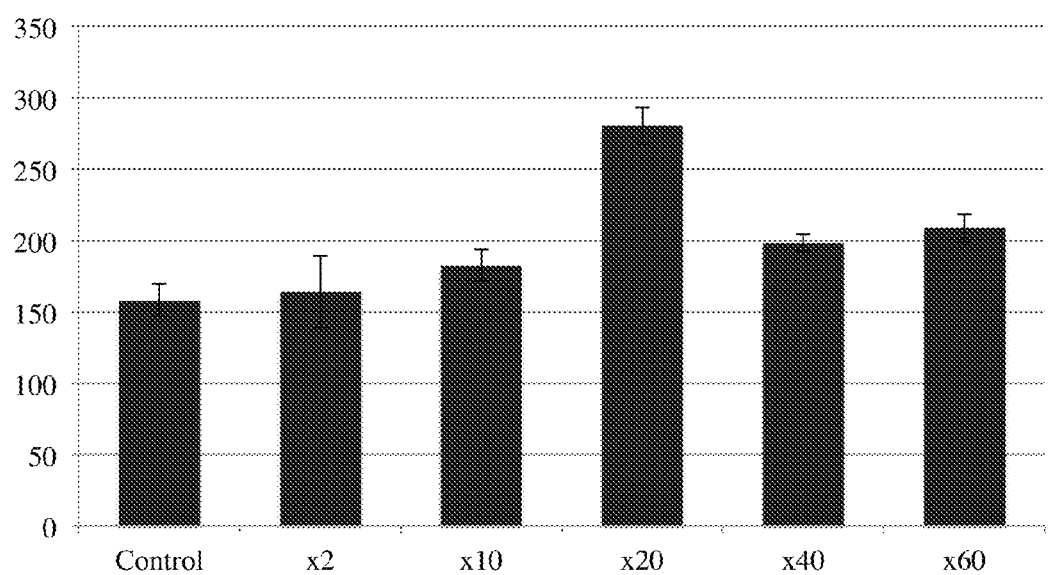

FIG. 24 shows a cell proliferation assay histogram one week post-reseeding. 20 cycles ($p=0.0002$), 40 cycles ($p=0.0056$) and 60 cycles ($p=0.0045$) of ultrasonication show statistically significant higher cell proliferation. The Nanogel with 20 cycles of ultrasonication showed the highest cell proliferation rate. Moreover, we did not observe macroscopic gelation at settings higher than 20 cycles.

Figure 25:
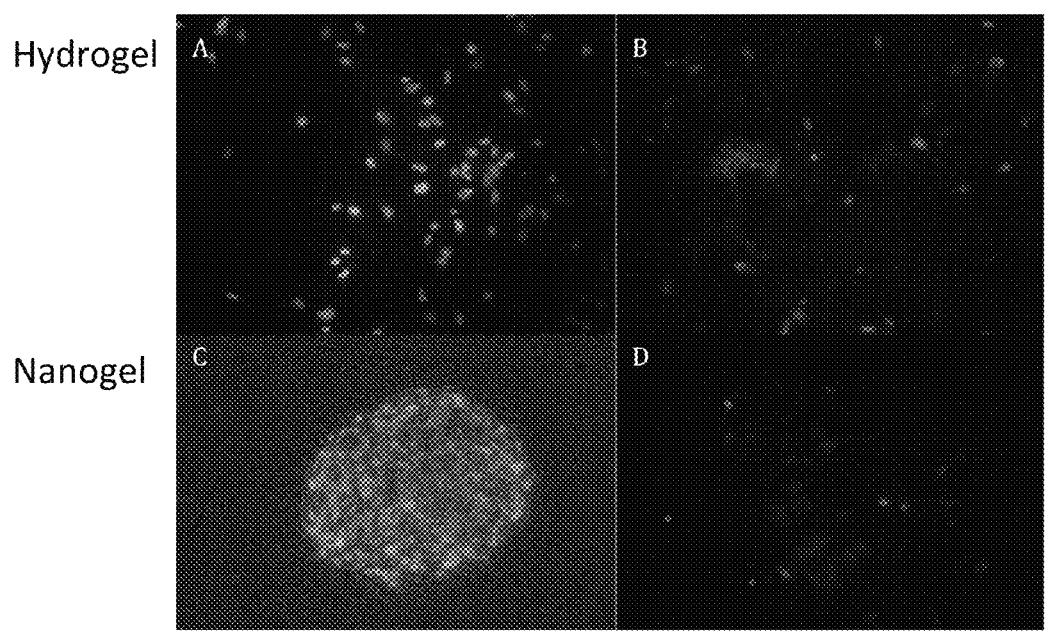

FIG. 25 shows live (green) and dead (red) Staining of human fibroblasts reseeded hydrogel (top row) and nanogel (bottom row) at 20× magnification on Day 7. The left column shows increased number of live cells in the Nanogel (C) while the right column shows decreased number of dead cells in the Nanogel sample (D) in comparison to the Hydrogel samples (A, B). Note the presence of cell cluster in the Nanogel.

Figure 26:
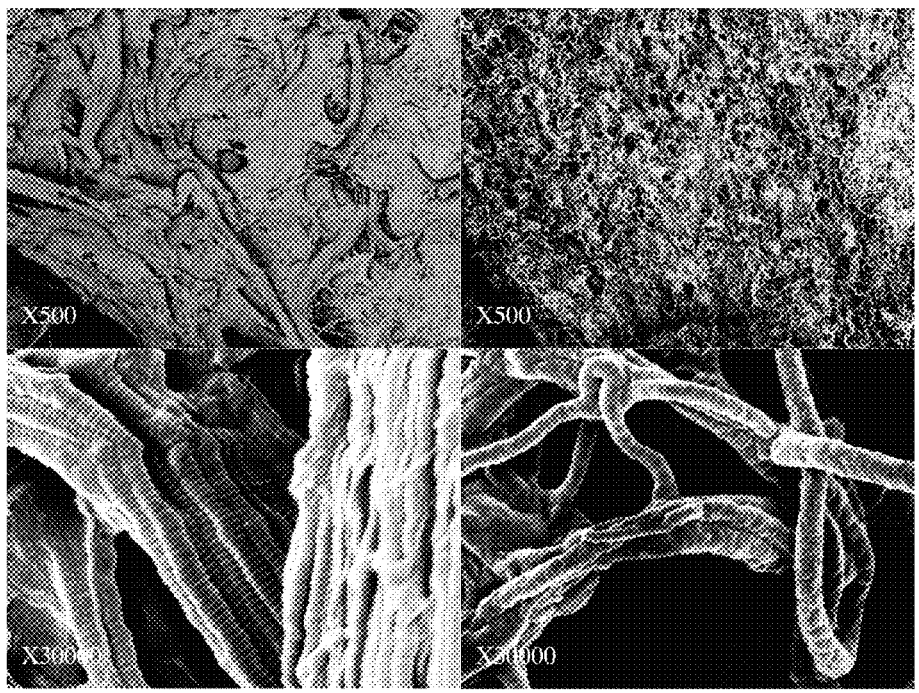

FIG. 26. Scanning electron micrographs show the collagen structure of the gels. The left column shows Hydrogel and the right column shows Nanogel. Note the increased porosity of the Nanogel sample when compared to the tight bundles of the Hydrogel.

Figure 27:
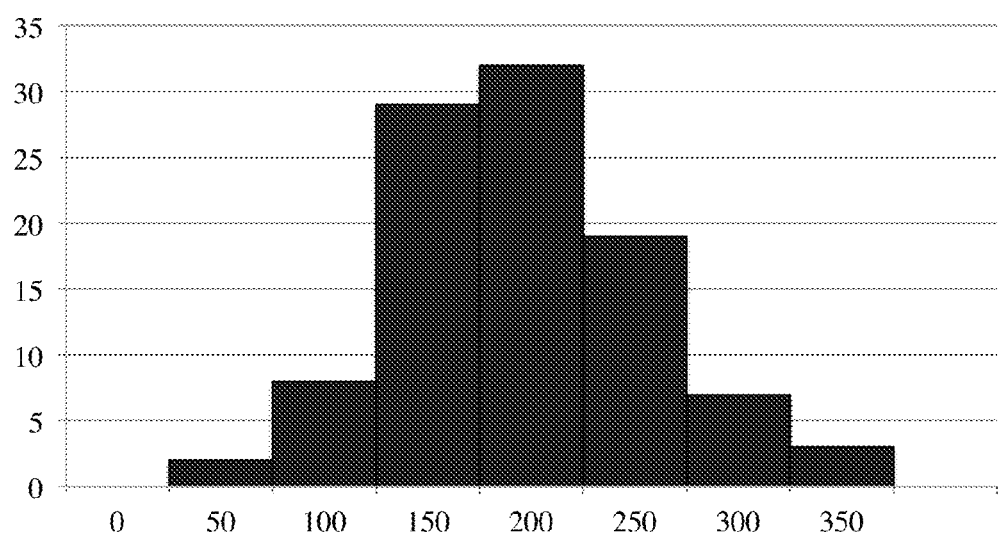

FIG. 27 illustrates a nanogel collagen fiber diameter frequency distribution histogram. The average collagen fiber diameter was 170±6 nm, confirming the nanosized network.

Figure 28:
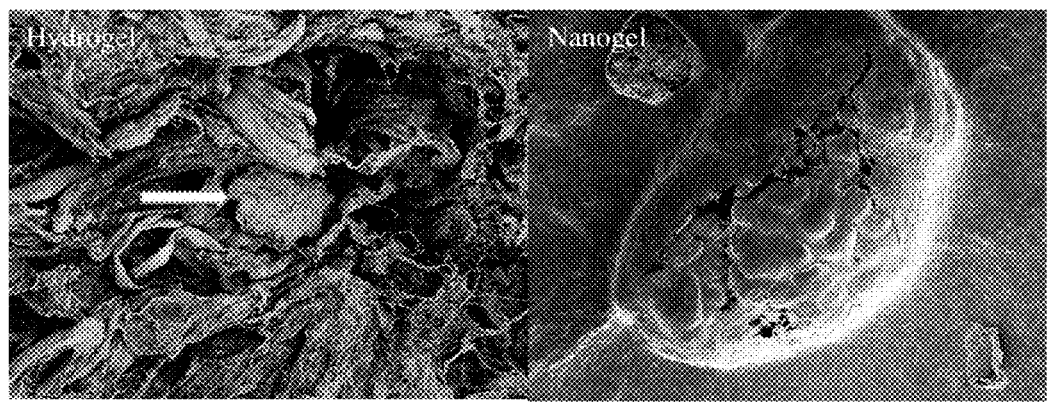

FIG. 28. Scanning Electron Micrographs show the cellular repopularization of the Hydrogel and the Nanogel, respectively, at same magnification (×500). Note the formation of big cell clusters in the Nanogel (right).

Figure 29:
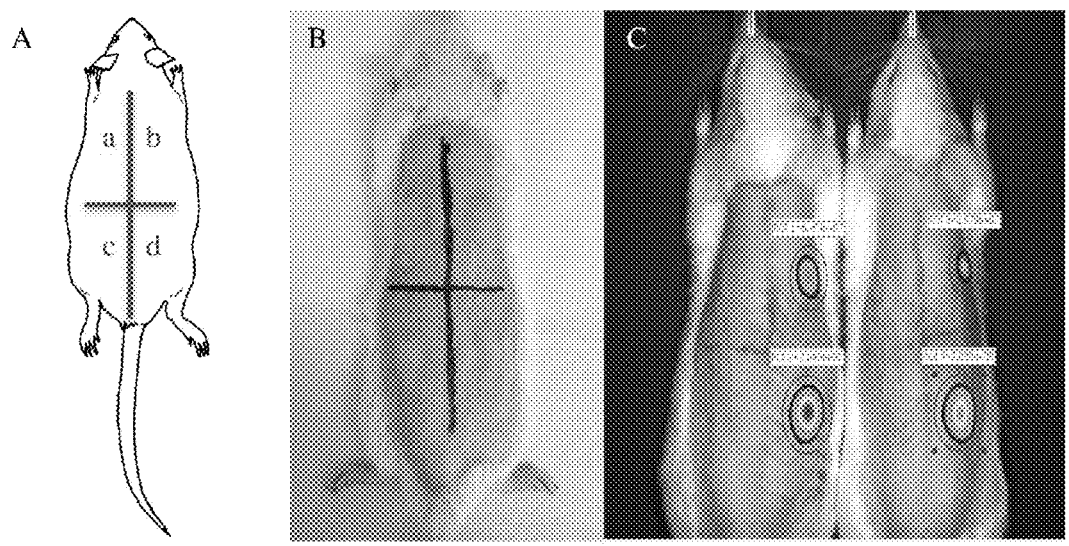

FIG. 29. In vivo Bioluminescent Assay. 1 mL of gel was injected at 4 different places in each rat's dorsum. Panel A: a: non reseeded Hydrogel; b: Rats Luciferase-firefly Transfected Fibroblasts reseeded Hydrogel; c: non reseeded Nanogel; d: Rats Luciferase-firefly Transfected Fibroblasts reseeded Nanogel. Panel B shows the injections area. Note that once injected, the nanogel stays in place and doesn't diffuse widely in the subcutaneous layer. Panel C demonstrates Bioluminescent Assay results in the first week.

Figure 30:
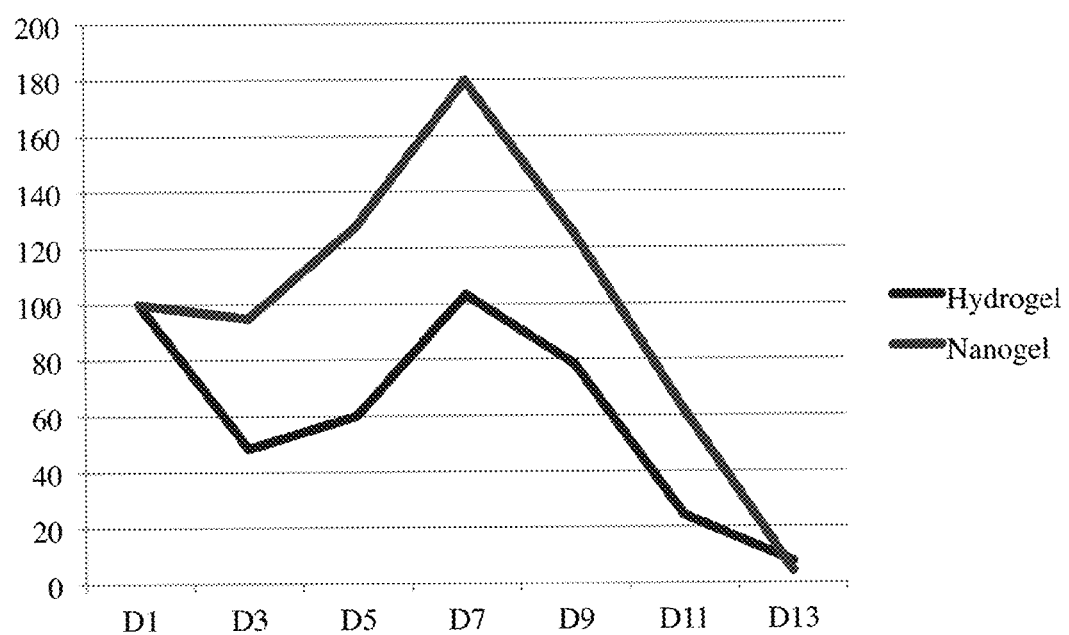

FIG. 30. Bioluminescence in vivo Cell Survival Evolution. n=4, no statistical significant difference was demonstrated (D3: p=0.0645; D5: p=0.15; D7: p=0.33; D9: p=0.22; D11: p=0.24).

Figure 31:
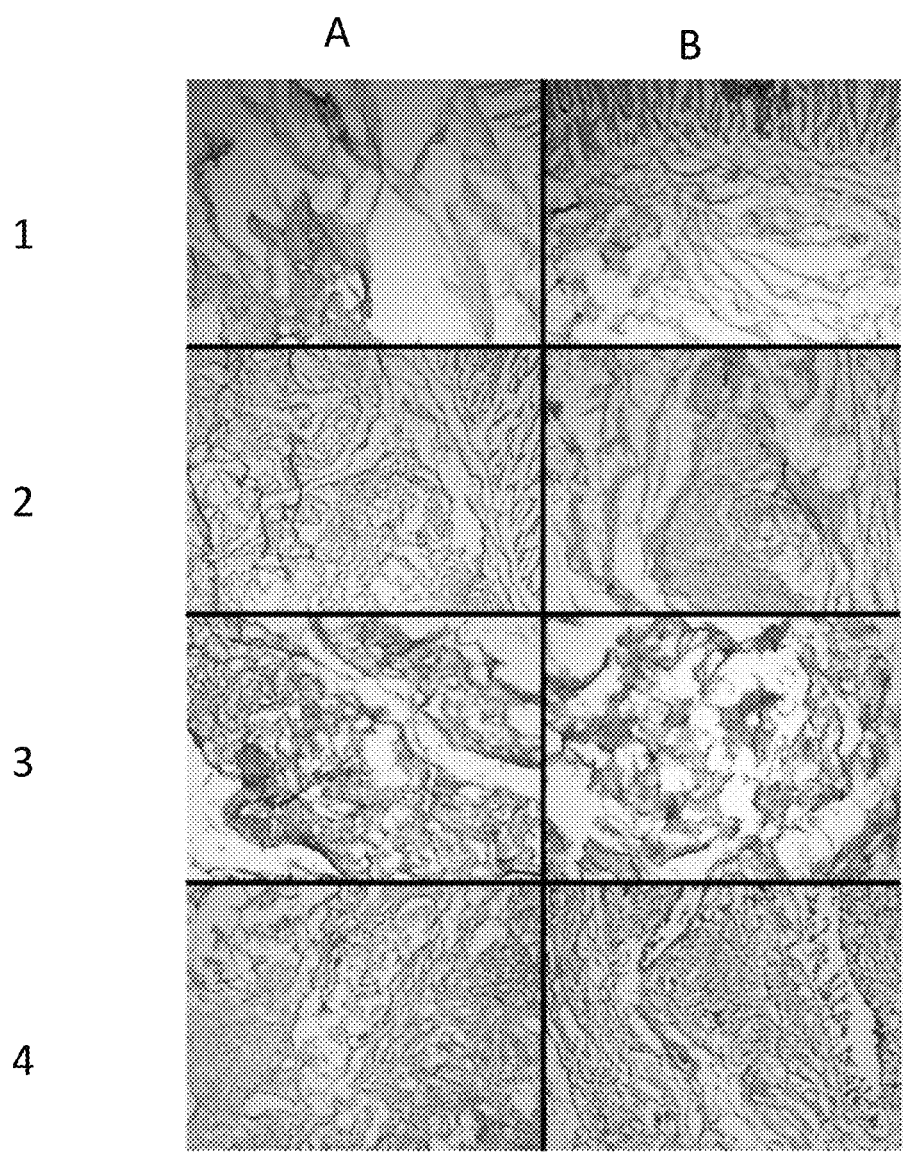

FIG. 31. H&E staining on Frozen Sections from in vivo samples, D7, after injection, with ×4 and ×10 magnification. Column A represents Hydrogel, column B represents Nanogel. First and third rows represent non reseeded samples, second and fourth rows represent Rats Fibroblasts reseeded samples. Note the presence of a vascular network in the reseeded Nanogel sample (B2 and B4).

7. DEFINITIONS

Before describing detailed embodiments of the invention, it will be useful to set forth definitions that are utilized in describing the present invention.

The practice of the present invention may employ conventional techniques of chemistry, cell biology, immunology, biochemistry, as well as of bone, joint, plastic and reconstructive surgery, which are within the capabilities of a person of ordinary skill in the art. Such techniques are fully explained in the literature. For definitions, terms of art and standard methods known in the art, see, for example, 'Current Protocols in Cell Biology', John Wiley & Sons (2007); 'Human Tendons', by Laszlo Jozsa & Pekka Kannus, Human Kinetics (1997). Each of these general texts is herein incorporated by reference.

Unless defined otherwise, all technical and scientific terms used herein have the same meaning as commonly understood by a person of ordinary skill in the art to which this invention belongs. The following definitions are intended to also include their various grammatical forms, where applicable. As used herein, the singular forms "a" and "the" include plural referents, unless the context clearly dictates otherwise.

The term "administration", as used herein, refers to introducing a composition, such as a tendon-derived extracellular matrix solution that polymerizes, i.e. gelates, at physiological temperature (body temperature, 37° C.), of the present disclosure into a subject. One preferred route of administration is to administer locally, meaning directly to the injured tendon or ligament via a needle or via an incision through the skin, i.e. percutaneously, so that the composition is not systemically distributed throughout the body.

The term "subject" refers to the host or recipient of the compositions of the present invention and includes humans as well as other mammals such as horses, cows, dogs.

"Donor", as used herein, refers to a mammalian cadaveric source for tendon connective tissue, as described herein, which can be from a human or animal source. Tendon connective tissue that was harvested from a donor can be "allogeneic", i.e., derived from a non-genetically identical member of the same species and, thus, be isolated from one subject and transferred, for example by injection, infusion or grafting, to another subject, particularly from one human to another human. Tendon connective tissue that was harvested from a donor can, furthermore, also be obtained from animal sources for use in the methods and compositions of the present invention. In such a case, the tissues are "xenogeneic", i.e., from a member of a different species. Preferred sources of xenogeneic connective tissues are pigs, horses, cows, sheep, rodents and dogs. In either case, all connective tissues are obtained from a fresh-frozen cadaveric donor. To obtain such connective tissues from a cadaveric donor, standard biopsy techniques known in the art may be employed.

"Therapeutically effective amount", as used herein, refers to an amount that provides the desired therapeutic effect of tendon or ligament tissue repair and regeneration in a mammalian subject.

The term "area of tendon or ligament injury", as used herein, refers to the site of the defect and designates (i) the actual site of the tendon or ligament injury as well as (ii) the zone that is directly adjacent to or surrounding of the actual site of the tendon or ligament injury.

An injectable composition, as used herein, refers to any material that can be made liquid enough or solubilized enough to be injected into a defect, i.e. an area of ligament or tendon injury, including an emulsion, liquid, particles and powder.

"Decellularization", as used herein, refers to the substantial (at least 75%), nearly complete (at least 95%) or complete removal of cellular components of tendon connective tissue by the use of physical and chemical means, or any combination thereof. It is understood that it is not necessarily preferred to achieve a maximally possible decellularization, if doing so negatively affects the biomechanical properties of the connective tissue. The optimum degree of decellularization will depend upon the biomechanical properties of the tissue and its intended use.

The storage (G') and loss (G") moduli for tendon hydrogels of the present invention represent the elastic and viscous properties of the gel.

"Tendon-muscle insertions", as used herein, refers to the site of connection between tendon and muscle and is also called the tendon junction site or myotendinous junction.

The "osteotendinous junction" is the site of connection between tendon and bone and is also called the tendon insertion site.

8. DETAILED DESCRIPTION

Embodiments of the present invention provide methods and compositions comprising decellularized extracellular matrix derived from tendon connective tissue for the minimally invasive, in-situ repair and regeneration of ligament and tendon injuries such as tears that resulted acutely from trauma or chronically from tendon or ligament overuse in a mammalian subject. The composition is in an injectable form below 25° Celsius and polymerizes upon administration to the defect of an injured ligament or tendon in a mammalian subject, where it fills out and conforms to the defect, thereby creating a three-dimensional tendon scaffold which attracts and facilitates migration of surrounding hosts cells into the scaffold microenvironment. The composition can also be supplemented with exogenous cells and/or therapeutic agents prior to administration to increase its in-situ therapeutic benefit for tendon or ligament repair and regeneration. Repair and regeneration of the injured ligament or tendon is ultimately achieved, when the tendon scaffold is replaced with the regenerated tissue.

8.1 Tendons

8.1.1 Tendon Composition

Tendons are strong bands of fibrous connective tissue that connect muscle to bone and are composed of parallel arrays of collagen fibers (mostly type 1 collagen) and elastin embedded in a proteoglycan-water matrix. The point of connection between muscle and tendon is the myotendinous junction, while the point of connection between tendon and bone is the osteotendinous junction. Most muscles have a single tendon distally, although some muscles have both a proximal and distal tendon. The basic functions of tendons, which are typically classified as flexors (flexing or bending a joint) or extensors (extending or straightening a joint) are to withstand tension and to allow transmission of forces created in the muscle to the bone, thus making joint and limb movements possible (Sharma & Maffulli, 2005; Kannus, 2000). This is made possible by a complex macro- and microstructure of tendons and tendon fibers, where collagen is arranged in hierarchical levels of increasing complexity, beginning with tropocollagen, a triple-helix polypeptide chain, which unites into fibrils, fibers (primary bundles), fascicles (secondary bundles), tertiary bundles, and the tendon itself. Soluble tropocollagen molecules form cross-links to create insoluble collagen molecules, which aggregate to form collagen fibrils. A collagen fiber is the smallest tendon unit that can be tested mechanically and is visible under light microscopy. Although collagen fibers are mainly oriented longitudinally, fibers also run transversely and horizontally, forming spirals and plaits (Sharma & Maffulli, 2005).

Healthy tendons have a fibro-elastic texture and show strong resistance to mechanical challenges. During various phases of movement, tendons are exposed to longitudinal as well as transversal and rotational forces, whereby the complex three-dimensional architecture of tendons provides critical support to prevent damage and disconnection of fibers. Muscles designed to create powerful, resistive forces such as the quadriceps and triceps brachii muscles, have short and broad tendons, while those that have to carry out subtle and delicate movements, like the finger flexor tendons, have long and thin tendons (Kannus, 2000). Intrasynovial tendons of the hand and the feet are surrounded by tendon sheaths or similar networks of connective tissue that contain the vascular, lymphatic and nerve supply to the tendon and whose main function is to minimize the friction between the tendon and its surroundings. Since proper movement and gliding of the tendon determines its efficiency, the tendon needs to be able to move freely and in an uninhibited manner. Tendon sheaths have two layers, an outer, fibrotic sheath, which consists of collagen fibrils and fibers, as well as an inner, synovial sheath, which consists of two sheets of synovial lining cells. These lining cells contain a thin film of fluid which is similar to the composition of the synovial fluid of a joint and which improves lubrication. The synovial lining cells are covered with fine collagen fibrils ('Human Tendons', by Laszlo Jozsa & Pekka Kannus, Human Kinetics (1997)). Synovial tendon sheaths are found in areas that often experience increased mechanical stress such as tendons of the hands and feet, where efficient lubrication is important (Sharma & Maffulli, 2006).

The tendon extracellular matrix consists of collagen fibers, elastic fibers, ground substance and inorganic components such as copper, manganese and calcium. The tendinous ground substance, which surrounds the collagen, consists of macromolecules such as proteoglycans and glycosaminoglycans (GAGs), structural glycoproteins, and a wide variety of other smaller molecules. The proteoglycans and glycosaminoglycans have a considerable capacity to bind water and are important for the biomechanical properties of tendon against shear and compressive forces.

8.1.2 Tendon Composition

Tenoblasts and tenocytes lie between the collagen fibers along the axis of tendon and are its major cellular components. Tenoblasts are immature tenocytes with higher metabolic rates that eventually mature into tenocytes. Chondrocytes are located at the sites of attachment and insertion into bone. Synovial cells of the tendon sheath as well as vascular cells form the remaining cellular components of a tendon. Tendons receive their blood supply from blood vessels entering from the myotendinous and osteotendinous junctions, the intratendinous vascular network and the synovial sheath.

Tenocytes synthesize collagen and all components of the extracellular matrix and are active in energy production, which can be aerobic as well as anaerobic. Compared to skeletal muscles, tendons and ligaments have a low metabolic rate, low oxygen consumption and a fairly well developed anaerobic energy production capacity. On the upside, a low metabolic rate allows tendons to maintain tension for prolonged periods without becoming ischemic and necrotic. On the downside, a low metabolic rate means that tendon injuries take a long time to heal.

8.1.3 Tendon Biomechanics

Tendons transmit force from muscle to bone, while at the same time acting as a buffer by absorbing external forces to limit tearing and other damage to the muscle. As a consequence, tendons have, by necessity, to exhibit high mechanical strength, good flexibility and high elasticity. The biomechanical properties of tendons are dependent on the collagen fiber diameter, fiber orientation, and collagen content. Tendons subject to multidirectional forces display collagen fiber bundles that lack regular orientation and the connective tissue is irregularly arranged. In contrast, tendons subject to unidirectional strain display collagen fiber bundles with mostly parallel orientation. The mechanical behavior of collagen depends on the number and types of intra- and intermolecular bonds. The tensile strength of a tendon is a function of its thickness and its collagen content.

8.1.4 Tests to Assess the Strengths of Tendons and Also Ligaments

In-vitro

In-vitro assessments. The biomechanical properties of an isolated tendon or ligament are tested in various in vitro tests. Test parameters that can be inferred from such tensile testing include stiffness, maximum load, and strain to maximal load. For the testing, the tendon or ligament tissue is elongated at a set rate, while the changes in force are recorded. The force is then plotted against displacement. Methods for testing of biomechanical properties include compression and tension testing. Exemplary methods that find wide-spread use for biomechanical strength testing include (a) Ultimate Failure Load. Ultimate Failure Load represents the maximum load (pull force on the tendon) that the tendon can withstand before breaking, measured in Newton (N). (b) Ultimate Tensile Stress. Ultimate Tensile Stress is a relative measurement that takes the physical properties of the graft into account. It is measured in $N/mm^2$ as the load per cross-sectional area of the tendon or ligament in question. (c) Stiffness. Stiffness represents the rigidity of the tendon that is the extent to which it resists deformation in response to the applied pull force at testing.

In-vivo assessment in subjects following tissue repair and regeneration using an injectable tendon hydrogel, as described herein. The assessment includes clinical evaluation of parameters such as 1) absence of pain, 2) speed of recovery to resume all-day activities such as walking and going up/down stairs as well as recreational sports such as running and biking, 3) less need for immobilization after injuries allowing for earlier active mobilization, and 4) strength and range of motion over affected joints. These variables, along with subjects' subjective satisfaction will be assessed in randomized clinical trials comparing the gel to conventional methods of treatment.

8.1.5 Tendons in the Upper Extremities

Finger Flexor Tendons.

Flexor pollicis longus tendon, flexor digitorum superficialis tendons and flexor digitorum profundus tendons belong to the group of finger flexor tendons.

Flexor Tendons of the Lower Arm.

Flexor carpi radialis tendon, palmaris longus tendon, flexor carpi ulnaris tendon and the common flexor tendon are flexor tendons of the forearm. The common flexor tendon is a tendon shared by a number of superficial flexor muscles in the forearm and attaches to the medial epicondyle of the humerus. Overuse of the common flexor tendon can lead to medial epicondylitis or golfer's elbow.

The common flexor tendon serves as the origin for a number of superficial muscles of the anterior compartment of the forearm such as the palmaris longus (a small tendon between the flexor carpi radialis and the flexor carpi ulnaris) or flexor digitorum superficialis (an extrinsic flexor muscle of the fingers at the proximal interphalangeal joints). The flexor digitorum profundus is another muscle in the forearm that flexes the fingers. It is an extrinsic hand muscle because it acts on the hand, while its muscle is located in the forearm and is a flexor of the wrist, midcarpal, metacarpophalangeal and interphalangeal joints.

Finger Extensor Tendons.

Extensor digiti minimi tendon, extensor digitorum communis tendons, extensor indicis tendon, extensor pollicis brevis tendon and extensor pollicis longus tendon belong to the group of finger extensor tendons. The abductor pollicis longus tendon, also found in the extensor group, is included in this category.

Tendons of the Arm and Shoulder.

The tendons of the rotator cuff muscles help to stabilize the shoulder, while the biceps tendon helps to bend the elbow and rotate the arm.

Extensor Tendons of the Forearm.

Extensor carpi ulnaris tendon; Extensor carpi radialis brevis tendon, extensor carpi radialis longus tendon and the common extensor tendon are extensor tendons of the forearm. The common extensor tendon originates from the lateral epicondyle and is often injured due to overuse, leading to lateral epicondylitis or tennis elbow.

8.1.6 Tendons in the Lower Extremities

The Achilles tendon, also called tendocalcaneus, is part of the posterior leg and is the thickest and strongest tendon in the body. It connects the superficial muscles of the posterior leg, plantaris, soleus and gastrocnemius (calf muscle) to the calcaneus (heel) bone. Albeit it is the largest and strongest tendon in the human body, the Achilles tendon is highly susceptible to acute and chronic injuries during athletic activities, since it needs to fulfill high functional demands during sports such as soccer, track and field, tennis, basketball and so forth. During sprinting exercises, the Achilles tendon is exposed to tensile forces that are about 10-12 times the body weight of the sprinting individual, while during jumping or cycling the tensile forces are about 6-8 times of the body weight.

Flexor Tendons of the Thigh.

The semitendinosis tendon, gracilis tendon, semimembranosis tendon are flexor tendons of the thigh. Semitendinosus is one of the hamstring muscles and functions both as flexor and extensor by helping to extend the hip joint and to flex the knee joint; it also helps to medially rotate the knee.

Patellar Tendon and Quadriceps Tendon.

The patella, also known as the knee cap, is embedded in and held in place by the patellar tendon on the tibial side (side of shin bone) and the quadriceps tendon on the femoral side (side of the thigh bone). The top of the patella attaches to the quadriceps muscle via the quadriceps tendon and the bottom of the patella attaches to the tibia via the patellar tendon, Flexor Tendons of the Leg.

Flexor digitorum longus tendons, flexor hallucis longus tendons, and tibialis posterior tendon are flexor tendons of the leg. Flexor digitorum longus, one of the muscles of the posterior compartment of the leg, functions to curl the toes and to stabilize the lower leg, while flexor hallucis longus, another muscle of the posterior compartment, performs plantar flexion of the big toe alone (downward movement of the toes). Tibialis anterior is situated on the lateral side of the tibia; it is thick, fleshy above, tendinous below and acts to dorsiflex (turn upward) and invert the foot. Tibialis posterior, a muscle of the posterior compartment of the leg, is the main stabilizing muscle of the lower leg and assists with foot inversion and ankle plantar flexion. Peroneus longus, and peroneus brevis are everters of the foot that secondarily plantarflex at the ankle.

Flexor Tendons of the Foot.

The flexor digitorum longus and brevis, flexor hallucis longus and brevis, and flexor digiti minimi brevis tendon are flexor tendons of the foot.

Extensor Tendons of the Leg.

Extensor digitorum longus tendons and extensor hallucis longus tendon are extensor tendons of the leg. The extensor digitorum longus tendons are located at the lateral part of the front leg and act to dorsiflex the foot as well as the toes and invert the foot. The extensor hallucis longus is part of the anterior leg and functions to extend the big toe, dorsiflex the foot, and assists with foot inversion. Tibialis anterior and peroneus tertius are extensor tendons of the leg that dorsiflex the foot at the ankle.

Extensor Tendons of the Foot.

Extensor digitorum longus and brevis tendons as well as extensor hallucis longus and brevis tendons are extensor tendons of the foot. The extensor digitorum brevis is a muscle on the dorsal (upper) part of the foot that functions to extend the smaller toes, while the extensor hallucis brevis, which is a muscle of the dorsum of the foot, acts to extend the big toe.

8.1.7 Acute Tendon Injuries and Chronic Tendon Injuries (Tendinopathies)

Particularly currently in an exercise-conscious and sports enthusiastic society, tendon disorders such as tendon injuries and tendinopathies occur frequently and in any age group, leading to weeks and months of pain, impaired physical activity and lengthy treatment that can range from physical therapy to surgical rehabilitation. Tendons and ligaments have an about 7.5 lower oxygen consumption than skeletal muscles due to a low metabolic rate and capacity to generate energy anaerobically which makes tendons and ligaments well suited to withstand and maintain tension. The low metabolic rate, however, also means that the healing process is slower than in skeletal muscle (Sharma & Maffulli, 2005).

Tendon injuries can be (i) acute strain injuries, tendon tears or full ruptures of the muscle-tendon units due to sudden, spontaneous impacts or laceration by a sharp object or (ii) chronic injuries (tendinopathies) due to tendon overuse without proper recovery time between uses and possible subsequent degeneration of the tendon tissue. Generally, acute tensile overload situations and overuse cause injuries to the musculotendinous junction, which manifest as sprains, strains and rupture, while injuries to the osteotendinous junction lead to avulsion fractures, bone detachment injuries and chronic enthesopathies, i.e. disorders of the tendon-bone attachment.

Tendon injuries manifest themselves usually through pain, particularly during sports-related activities which might have contributed to the injury at the first place, then focal tenderness with pain radiating from particular trigger points and decreased strength and ability to move.

Tendon injuries, that frequently occur in the course of sports activities and for which the methods and compositions of the present invention are particularly well suited, include (i) Achilles tendon injuries, generally due to the performance of high-force movements and spontaneous change of directionality, as it is the case in soccer, track and field or tennis (Kannus & Natri, 2007); (ii) rotator cuff injuries, usually caused by motions that require forceful pulling motions or repetitive overhead motions, as they occur in sports activities such as tennis, martial arts, boxing, swimming, golf, cheerleading or throwing activities; (iii) common flexor tendon injuries such as medial epicondylitis of the elbow, the so-called 'golfer's elbow', and common extensor tendon injuries such as lateral epicondylitis of the elbow, the so-called 'tennis elbow'; (iv) patellar tendon and quadriceps tendon injuries that are concomitant with patellar dislocation that often occurs during sports activities that involve sudden and forceful knee rotation, such it is the case in soccer, tennis, basketball and martial arts.

8.1.8 Healing Process in Tendons: Need to Maintain Normal and Organized Tendon Tissue Dependent on the extent of the injury, likely excluding a healing in cases of complete ruptures, tendons have a capacity to heal on their own. The process of tendon healing occurs in several phases. After the initial inflammatory phase within the first 24-72 hours, the remodeling phase begins within an increased collagen synthesis. After approximately six weeks, the modeling stage begins with high collagen synthesis and high tenocyte metabolism, in the course of which the injured tissue becomes filled with disorganized tissue and gradually changes from cellular to fibrous and eventually to scar-like tissue. As a consequence, the structural organization and the mechanical properties of the healing tissue are altered and the tendon's capability to withstand force is compromised. Although the tensile strength of the healing tendon reportedly improves over time, it does not return to its original levels for about one year or longer (Lin et al., 2004).

Not only is clinical tendon repair and regeneration, for which the methods and compositions of the present invention are well suited, important to accelerate a subject's recovery and ability to use the healed tendon, it is also critical to rebuild the injured tendon in a way that it regains the structural and functional characteristics of a normal, healthy tendon with its full range of motion and tensile strength.

8.2 Ligaments

Hamstring or medial collateral and lateral collateral ligaments, anterior or posterior cruciate ligaments of the knee are examples of important ligaments of the body.

Ligaments, similar to tendons, are strong bands of fibrous connective tissue consisting of fibers made mainly out of type 1 collagen. In contrast to tendons, which connect muscle to bone, ligaments connect bones to other bones across a joint. Some ligaments limit the mobility of a joint or prevent certain movements altogether. Ligaments are elastic and lengthen under tension, unlike tendons, which are inelastic.

Capsular ligaments are part of the articular capsule that surrounds synovial joints. They act as mechanical reinforcements. Extra-capsular ligaments provide joint stability. Intra-capsular ligaments, also provide stability, but permit a far larger range of motion. Cruciate ligaments occur in pairs (anterior and posterior).

8.2.1 Ligaments of the Head, Neck and Chest

Ligaments of the head, neck and chest, include the cricothyroid ligament, periodontal ligament and suspensory ligament of the lens, which all are ligaments of the head and neck, while the suspensory ligament of the breast is a ligament of the human thorax.

8.2.2. Ligaments of the Upper Extremities

The radial and ulnar collateral ligaments of the interphalangeal and metacarpophalangeal joints are ligaments of the human hand. The palmar radiocarpal ligament, dorsal radiocarpal ligament, ulnar collateral ligament and radial collateral ligament are ligaments of the human wrist. The acromioclavicular ligaments surround and support the acromioclavicular joint which is the connection between the scapula and the clavicle. The coracoclavicular ligaments hold the clavicle down by attaching it to a bony knob on the scapula called the coracoid process. The scapholunate interosseous ligament is a broad ligament connecting the scaphoid bone to the lunate bone. There are multiple additional intrinsic and extrinsic wrist ligaments that contribute to stability of the wrist.

8.2.3. Ligaments of the Lower Extremities

Ligaments of the lower extremities include the anterior cruciate ligament (ACL), lateral collateral ligament (LCL), posterior cruciate ligament (PCL), medial collateral ligament (MCL), which all are main ligaments of the human knee. In the quadruped from, the ACL is referred to as the cranial cruciate ligament (CrCL), while the PCL is referred to as the caudal cruciate ligament (CaCL).

8.2.4 Ligaments of the Pelvis

The anterior sacroiliac ligament, the posterior sacroiliac ligament, the sacrotuberous ligament, the sacrospinous ligament, the inferior pubic ligament, the superior pubic ligament and the suspensory ligament of the penis are ligaments of the human pelvis.

8.2.5 Ligament Injuries and Problem in Ligament Repair

Ligament injuries, which are often acquired during weight-bearing sports activities such as downhill skiing, running, jumping and the like, can lead to instability of the joint that the ligament is supposed to stabilize. Instability of a joint can lead to cartilage wear over time and eventually to osteoarthritis. Therefore ligament injuries need to be taken seriously and repaired.

8.3 Tendon-Derived Extracellular Matrix Hydrogel for Tissue Repair and Regeneration The thermosensitivity and solid-liquid characteristics of the tendon extracellular matrix solution, being liquid at a cold temperature up to room temperature (4-25° C.) and gelating at physiological body temperature, at around 37° C., allow easy and quick administration of the solution via injection or infusion, while the gelation in situ, upon administration into the area of the tendon or ligament defect, i.e. the site of injury, of a subject allows the formation of a three-dimensional tendon support scaffold. Since this resulting tendon support scaffold/tendon hydrogel is based on decellularized materials from tendon tissue, it replaces 'like with like', since the scaffold already possesses the mix of non-cellular components that matches that of the native tissue (tendon or ligament) such as various types of collagen fibers, hyaluronic acid, fibronectin, laminin, carbohydrate polymers, polysaccharides and sulfates.

The administration of the solubilized tendon-derived extracellular matrix into the area of ligament or tendon defect or injury is preferably carried out via injection with a needle (for example, 25 gauge). It is considered a minimally invasive procedure, since it does not require a surgical procedure (including anesthesia) and can be carried out during an office visit. This ensures quick attendance to the tendon or ligament injury and, consequently, accelerates a subject's recovery from the injury.

Upon gelation, the solubilized tendon-derived extracellular matrix conforms to the three-dimensional space of the tendon or ligament defect that resulted from the injury and so facilitates in situ regeneration by means of three-dimensional (3D) guided tissue regeneration, accelerating ligament and tendon healing, as shown in Example 2. Thus, the repair and regeneration of the tissue defect in the injured ligament or tendon is aided by the three-dimensional support scaffold of the tendon-derived hydrogel ('tendon hydrogel').

Furthermore, upon gelation and adaption/conformation to the 3D space of the tendon or ligament defect, the tendon-derived hydrogel provides a supportive nanostructure for renewed organization of collagen fibers that became disorganized during the tendon or ligament injury. The tendon-derived hydrogel, furthermore, creates a structure suitable for host cell infiltration, i.e. infiltration of fibroblasts, tenoblasts and tenocytes from the host, and tissue regeneration. Likewise, cells such as stem cells, progenitor cells or fibroblasts, and therapeutic agents can be added to the solubilized tendon-derived extracellular matrix prior to injection and prior to gelation in order to increase its in-situ therapeutic benefit for tissue regeneration.

In certain embodiments, the therapeutic agent can be a growth factor such as basic fibroblast growth factor (bFGF), vascular endothelial growth factor (VEGF), hepatocyte growth factor (HGF), insulin-like growth factors 1 and 2 (IGF-1 and IGF-2), platelet derived growth factor (PDGF), or stromal cell derived factor (SDF-1).

Alternatively, growth factors can be supplemented through autologous platelet-rich plasma (PRP) enrichment of the tendon-derived hydrogel to stimulate and accelerate tissue regeneration. PRP refers to autologous plasma with platelet concentrations at particular levels above baseline values (Hall et al., 2009).

In other embodiments, the therapeutic agent is a small molecule or protein exhibiting antibacterial effects in order to ameliorate a risk of infection that may occur concomitant with the tendon or ligament injury. Examples of antibiotics suitable as therapeutic agents include (i) aminoglycosides such as gentamicin, streptomycin, tobramycin, (ii) glycopeptides such as vancomycin, (iii) lincosamides such as clindamycin, (iv) macrolides such as azithromycin, (v) polypeptides such as bacitracin, (vi) quinolones such as ciprofloxacin, (vii) tetracyclines such as doxycycline, tetracycline, and other categories of antibiotics that can be administered into the defect, either combined with the tendon-derived extracellular matrix solution, administered prior to the administration of the tendon-derived extracellular matrix or administered after the tendon-derived extracellular matrix has been administered, and can exert a localized effect.

In further embodiments, the therapeutic agent is a small molecule or protein exhibiting analgesic effects in order to ameliorate pain that may occur concomitant with the tendon or ligament injury. Examples of analgesics suitable as therapeutic agents include (i) non-steroidal anti-inflammatory agents such as ibuprofen and naproxen as well as (ii) local anesthetics such as lidocaine and bupivacaine.

8.4 Utility of Injectable Tendon-Derived Extracellular Matrix that Gelates In Situ to a Tendon-Derived Hydrogel for In-Situ Tendon and Ligament Repair and Regeneration Since tendon disorders such as tendon injuries as well as tendinopathies and ligament injuries occur frequently and in any age group, and lead to weeks and months of pain, impaired physical activity and lengthy treatment, ranging from physical therapy to surgical rehabilitation, compositions such as the described tendon-derived hydrogels that support the healing process and that can be administered to the injured tissue without a major surgical step, as described in the present invention, are of high utility and benefit. This is evidenced by a shortened healing time as well as tissue (tendon and ligament) regeneration that enables to regain the original strength of the tendon and ligaments. Due to its thermosensitive properties solubilized tendon-derived extracellular matrix remains liquid and injectable in the temperature range of about 4-25° C. Upon injection of the solubilized tendon-derived extracellular matrix into a bodily space such as into the area of a ligament or tendon injury, the solubilized tendon extracellular matrix—at the body temperature of about 37° C.—gelates within minutes into a tendon-derived hydrogel, as described in Examples 1 and 2.

The hydrogel then fills out and conforms to the defect. It, thus, creates a scaffold which attracts and guides the settling of new tenoblasts, tenocytes and fibroblasts inside the defect for repair and regeneration of the injured ligament or tendon.

In some cases of ligament or tendon injury, a one-time administration of a therapeutically effective amount of a tendon-derived hydrogel might be sufficient to treat the defect. In other cases, repeated administration of therapeutically effective amounts of a tendon-derived hydrogel, within the time period of several days, weeks or months, might be needed to treat the defect. In further cases, repeated administration of therapeutically effective amounts of a tendon-derived hydrogel, within the time period of several days, weeks or months, might be carried out to improve clinical efficacy.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. In the following, experimental procedures and examples will be described to illustrate parts of the invention.

9. EXAMPLES

The following examples are put forth as to provide those of ordinary skill in the art with a complete disclosure and description of how to make and use the present invention; they are not intended to limit the scope of what the inventors regard as their invention. Unless indicated otherwise, parts are parts by weight, molecular weight is average molecular weight, temperature is in degrees Centigrade, and pressure is at or near atmospheric.

I. Composition or In-Situ Repair and Regeneration of an Injured Ligament or Tendon Comprising Decellularized Extracellular Matrix Derived from Tendon Connective Tissue, Said Composition being in Injectable Form Below 25 Degree Celsius and Forming a Gel at Physiological Temperature Example 1: Injectable Human Tendon-Derived Hydrogel as a Scaffold for In-Situ Guided Tissue Regeneration in the Musculoskeletal System 1.1 Experimental Procedures Tissue Decellularization and Material Processing.

Human flexor digitorum profundus (FDP), flexor digitorum superficialis (FDS) and flexor pollicis longus (FPL) tendons were harvested from fresh-frozen human cadaveric forearms (Science Care, Phoenix, Ariz.). Epitenon, synovial sheath, and muscle tissue were meticulously debrided. Distally, FDS tendons were transected 2 cm proximal to the chiasma, and FDP and FPL tendons were transected 1 cm proximal to the osteotendinous junction. The tendons were then decellularized following a previously reported protocol (Pridgen B C et al., 2011). In brief, scaffolds were treated with 0.1% ethylenediamine-tetraacetic acid (EDTA) for 4 hours followed by 0.1% sodium dodecyl sulfate (SDS) in 0.1% EDTA for 24 hours at room temperature with constant agitation. Scaffolds were washed in PBS (also referred to as saline herein) and stored at −80° C. The decellularization protocol was used as sole sterilizing agent in these experiments.

The frozen decellularized material was then lyophilized, and thereafter cut into smaller tendon pieces and milled into a fine powder using a Wiley Mini Mill (Thomas Scientific, Sedesboro, N.J., USA). The powder was stored at 4° C. until needed for use. A DNA assay along with routine H&E histology and SYTO green-fluorescent nucleic acid staining was used to quantify the effectiveness of decellularization of tendons. This is described in detail in a previous publication (Pridgen et al., 2011). In short, DNA was extracted from lyophilized tendons using a DNeasy kit (QIAGEN). The concentration of the extract was determined using an ultraviolet spectrophotometer (Biophotometer 22331; Eppendorf) at a wavelength of 260 nm. The concentration of the samples was calculated by software on the spectrophotometer using a known extinction coefficient for dsDNA.

Extracellular Matrix (ECM) Gel Formation.

The powder of decellularized and lyophilized ground tendons, which was produced as described above, was then solubilized and enzymatically digested by adding a 1 mg/ml solution of pepsin (Sigma, St Louis, Mo.) in HCl and water such that the final concentration of material was 10, 20 and 30 mg/ml (1-3% respectively, dry weight). Optimal pH for pepsin digestion was explored and set to pH 2.2 (Bohak, 1969). Increasing molarity of HCl is needed to accomplish optimal digestion with increasing concentration of tendon powder (see Table 1). The material was digested for up to 72 h (12, 24, 36, 48 and 72 h) at room temperature with constant stirring. The extracellular matrix solution (ECM solution) was checked for pH and homogeneity under a microscope every 12 h to optimize the conditions for digestion. For the in vivo experiments and reseeding of 2% gels in vitro, the digestion time was set to 24 h to ensure complete digestion.

After complete and optimal digestion was confirmed, the salt concentration was adjusted with the addition of 10×PBS (1/10 of final neutralized volume), while cooled on ice. Pepsin activity was then completely reversed by adding of NaOH to increase the pH>8, before the final solution pH was neutralized to a pH of 7.4 by addition of HCl. The final mixture was then ready for injection or in vitro experiments. When placed in an incubator at 37° C. it was allowed to gel for 20-60 minutes at 37° C. Gelation was confirmed macroscopically and with rheology (see below and FIG. 1).

Optimal storage conditions of the ECM solution was explored. The ECM solution was stored as neutralized samples with a pH 7.4, and as acidic samples with a pH 2.2 under different conditions (4°, −80° and lyophilized). The acidic samples were neutralized after storage, but prior to gelation at 37°. Gelation was observed on day 1, 7, and 10 over 30 minutes and recorded as (−) no gelation, (+/−) weak gelation, (+) gelation.

Evaluation by Mass Spectrometry.

Samples were prepared using a FASP (Filter aided proteome preparation) (Wisniewski et al., 2009) protocol, where the sample was solubilized in SDS, DTT and Tris-HCL and digested overnight by trypsin. The peptides were loaded onto a self-packed fused silica C18 analytical column, interfaced by a Bruker Michrom Advance (Auburn, Calif., USA) source with a flow rate of 600 nL/min and a spray voltage of 1.7 kV. The mass spectrometer was a LTQ Orbitrap Velos, Thermo Scientific (Vancouver, Canada), set in data dependent acquisition mode fragmenting the top 12 most intense precursor ions. The RAW data was converted to mzXML format and database searched against the human uniprot-sprot database using Sequest on a Sorcerer platform. The data was visualized using Scaffold 3, Proteome Software (Portland, Oreg., USA).

Rheology: Storage Modulus, Temperature Characteristics.

Rheological measurements were made using a TA Instruments ARG2 Rheometer. Two parallel steel plates (40 mm diameter) at 100 μm gap height were used on 500 μl of tendon-derived hydrogel in different concentrations, performed 24 hours after the extracellular matrix solution was allowed to gelate. The setup was such that the sample completely filled the gap between the rheology plates. For each condition, the storage modulus (G') and loss modulus (G") over frequencies of 0.1-10 rad s-1 (frequency sweep) were recorded for every gel condition in triplicate and plotted. To document gelation properties at increasing temperature (temperature sweep), the peltier probes of the rheometer were preheated to 25° C. Measurements of samples of extracellular matrix solution that had not been allowed to gelate were recorded at 1 rad sec-1 at increasing temperature, 2° C. per minute until 37° C. was reached. Temperature was maintained at 37° C. for 24 minutes until the gel had polymerized and the modulus had stabilized.

Scanning Electron Microscopy.

Samples were fixed from 24 hrs to 4 days at 4° C. with 4% paraformaldehyde and 2% glutaraldehyde in 0.1M sodium cacodylate buffer (pH 7.2), rinsed in the same buffer and post-fixed for 1 hr with 1% aqueous $OsO_4$. After dehydration in an ascending ethanol series (50, 70, 90, 100%; 15 min each) samples were dried with liquid $CO_2$ in a Tousimis Autosamdri-815B apparatus (Tousimis, Rockville, Md., USA), mounted on adhesive copper tape on 15 mm aluminum stubs (Ted Pella, Redding, Calif.), and sputter-coated with 50 A of Au/Pd using a Denton DeskII Sputter Coater. Visualization was performed with a Hitachi S-3400N Variable Pressure (VP) SEM operated at 15 kV, working distance 7-8 mm, and secondary electron (SE) detection under high-vacuum conditions (<1 Pa). High-resolution images of collagen fibrils were captured with a Zeiss Sigma Field Emission SEM operated at 3 kV and using Inlens SE detection. For VP-SEM application scaffolds with and without cells were visualized fully hydrated with variable pressure (50-60 Pa) and coldstage control (−25° C.) after aldehyde-fixation, and additional osmication of scaffolds with cells was performed (Joubert, 2009).

Cell Culture and Scaffold Reseeding.

Commercially obtained adipo-derived stem cells (ASCs) (up to passage 4, Poietics PT-5006 cryopreserved adipoderived stem cells, Lonza, Walkersville, Md., USA) were cultured in ADSC-BM medium (Lonza, Walkersville, Md., USA) augmented with 10% FCS. Cells were grown to confluence at 37° C. in a humidified tissue culture chamber with 5% carbon dioxide. Reseeding of the ECM solution was performed both onto preformed gel (a), and by mixing cells into the ECM solution before gelation (b). (a) The ECM solution was first allowed to gel for 1 h in a 48 well plate at 37° C. A cell suspension containing $5 \times 10^4$ cells/0.2 ml was placed on top of the preformed gel, and incubated overnight. (b) Seeding was also performed by mixing a cell suspension of $5 \times 10^4$ cells/0.2 ml with 0.5 ml ECM solution. The mix was placed in a 48 well plate and allowed to gel for 1 h at 37° C., then 0.5 ml medium was added. Cell culture medium was changed every other day for both seeding protocols. Cells were stained with SYTO Green or using a live dead assay on day 5 to check for viability on the gel surface and inside the gel.

In Vivo Application.

8 Wistar rats (mean weight 280 g) were used as recipients for injections of solubilized tendon extracellular matrix for subsequent gelation in situ, i.e. at and around the injection site. The rats were anesthetized with isofluorane in a prone position. Dorsal hair was shaved and the animals were marked with a permanent marker to assign four injection sites. Under sterile conditions, 1 ml of 2% solubilized tendon extracellular matrix was injected subcutaneously with a 25 G needle and syringe (FIG. 7) for subsequent gelation in situ. After the injections, all animals were housed at 21° C. in a 12-hour light and dark cycle and were given food and water ad libitum.

Gel specimens were harvested at 3 days, 7 days, 14 days and 21 days. One sample at each time point was used for measurement of size and subsequent SEM. The three other samples were used for histology. Formalin-fixed, paraffin-embedded (FFPE) sections (5 µm) were stained with hematoxylin and eosin (H&E, Sigma) for assessment of seeding efficacy and scaffold morphology. All histological images were taken with an inverted microscope (Nikon TS100, Nikon, Melville, N.Y.).

For macrophage staining, a mouse anti-rat CD68 primary antibody was used (Santa Cruz Biotechnology). Rat spleen was used as a positive control. Sections were also counterstained with Propidium Iodine (PI) to assess for cell infiltration. Whole tissue mounts were divided longitudinally and immersed in SYTO green (Invitrogen) nucleic acid stain at 1:2000 dilution in DI water for 20 min. Reseeded gels were then placed on coverslips and imaged. Separate images were obtained for the outer convex scaffold surface and the inner cut (core) surface.

Live/Dead assay (Invitrogen) was performed on reseeded gels at 5 days, on constructs where adipo-derived stem cells (ASCs) had been premixed with solubilized tendon extracellular matrix prior to gelation at 37° C. This assay was performed to assess the ratio of viable to nonviable cells. Gels 5 days post reseeding were labeled with Live/Dead stain and incubated for 20 minutes.

1.2 Tendon Extracellular Matrix (ECM) Gel Formation: pH and Digestion Time

Hydrogels were successfully prepared from decellularized and ground human tendons (Human flexor digitorum profundus (FDP), flexor digitorum superficialis (FDS) and flexor pollicis longus (FPL) tendons), that had been harvested from human cadavers and immediately fresh frozen at −80° C. and reconstituted to obtain solubilized tendon extracellular matrices with concentrations ranging from 1-3% (v/v). Increasing extracellular matrix concentration provided a more rigid gel structure that was easier to handle. The 2% solubilized tendon extracellular matrix produced a gel that showed an optimal balance between handling properties, structural rigidity and permeability to seeded cells. Therefore, experiments on reseeding, storage and in vivo experiments were preferably conducted using the 2% solubilized tendon extracellular matrix concentration.

Figure 1:
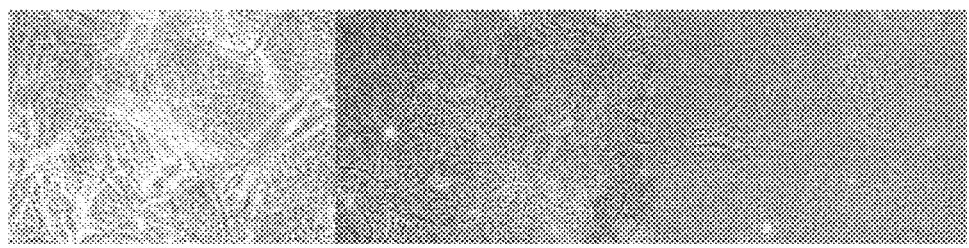

Optimal HCl molarity and digestion time [in minutes] was determined based on microscopic appearance of the degree of ECM digestion (see Table 1 and FIG. 1).

TABLE 1

Optimal pH for pepsin digestion was explored. Increasing molarity (N) of hydrochloric acid (HCl) is needed to accomplish optimal digestion with increasing concentration of tendon powder. This is an essential step in the gel making process as complete digestion of the decellularized lyophilized powder is needed for the extracellular matrix (ECM) solution to hold its thermoregulatory gelation properties so that it is liquid at 4-25° C. and gelates at around 37° C.

| molarity | 1% | 2% | 3% |
|----------|-----|------|------|
| 0.01N | 2.5-3.0 | 3.5-4.0 | 4.0-4.5 |
| 0.02N | 1.5 | 2.5-3.0 | 3.5-4.0 |
| 0.03N | | 2.0-2.5 | |
| 0.05N | | 1.5-2.0 | 1.5 |
| 0.1N | | 1.0 | |

Figure 2:
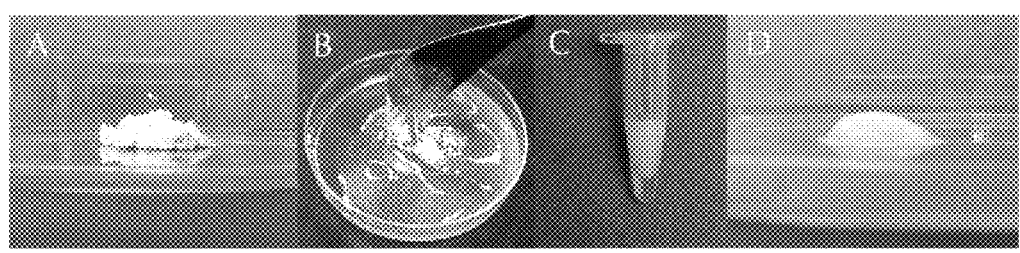
FIG. 2 illustrates, as detailed in Example 1, the production of injectable (25 G cannula) tendon extracellular matrix (ECM) solution from ground tendon (A) and enzymatic digestion (B, enzyme used here was pepsin) at low pH and, subsequently, the formation of the hydrogel (C) following incubation for 20 minutes at 37° C. (D) shows the hydrogel poured and gelled on a petri dish.

The optimal conditions consisted of the ECM powder digested over 24 h at pH around 2.2, with gelation macroscopically complete after 20 minutes in 37° C. (FIG. 2). Once solubilized, the tendon extracellular matrix solution remained liquid at 4° C. To induce gelation in vitro, samples of solubilized tendon extracellular matrix were placed in an incubation chamber at 37° C. Gelation was observed macroscopically within 20 minutes. The tendon extracellular matrix solution showed a gradual decrease in gelation characteristics after storage at various conditions over time, unless the samples were stored at about pH 2.2. At pH 2.2, the solubilized tendon extracellular matrix could be stored for prolonged periods, with unchanged gelation properties following neutralization to pH 7.4 (Table 2).

TABLE 2

Comparison of tendon extracellular matrix gelation properties stored at pH 2.2 v. pH 7.4

| | | Day 1 | Day 7 | Day 10 |
|---|---|---|---|---|
| pH 7.4 | 4° | + | +/− | − |
| | −20° | + | | − |
| | −80° | + | | − |
| | Lyophilized | + | | − |

TABLE 2-continued

Comparison of tendon extracellular matrix gelation properties stored at pH 2.2 v. pH 7.4

|  |  | Day 1 | Day 7 | Day 10 |
|---|---|---|---|---|
| pH 2.2* | 4° | + |  | + |
|  | −20° | + |  | + |
|  | −80° | + |  | + |
|  | Lyophilized | + |  | + |

Mass Spectrometry.

Figure 3:
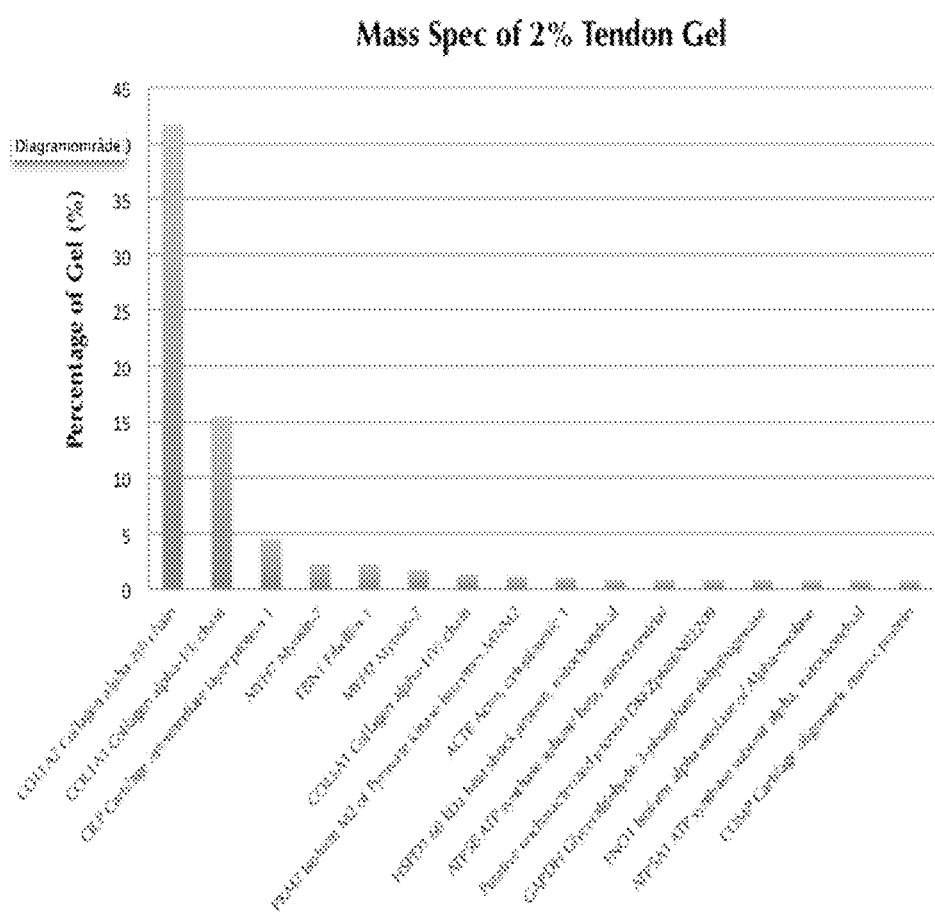
FIG. 3 shows the result of a proteomic analysis of an extracellular matrix solution, which was prepared as described in Example 1, via mass spectrometry, where the amount of detected proteins (collagens and extracellular matrix proteins) is presented as percentage of total content (%).

Proteome analysis of the tendon-derived extracellular matrix solution and resulting tendon-derived hydrogel through filter-aided sample preparation (FASP) and mass spectroscopy yielded identification of the most abundant 150 proteins, of which Collagens represented more than 55% of the sample (FIG. 3). Collagen 1A2 was the most prominent protein (42% of total content) followed by Collagen 1A1 (15%). All other proteins had a less than 5% representation in the assay. The 16 proteins with highest representation are listed in FIG. 3.

Rheology.

The rheological properties of the tendon extracellular matrix solution were determined through triplicates of the storage (G') and loss (G") moduli as shown in FIG. 4a. G' at 1 rad/s was 213.1±19.9 and G" 27.1±2.4. A temperature sweep was performed to evaluate the effect of temperature and time on modulus. Both the storage modulus G' and the loss modulus G" remained stable, approximately one order of magnitude lower than after gelation (FIG. 4b) as the temperature was slowly increased from 25° C. to 37° C. At 37° C., the tendon extracellular matrix solution was allowed to gel without further increases in temperature. The fact that the tendon extracellular matrix solution only forms a tendon hydrogel at body temperature is a key feature of this hydrogel. The ECM solution can thus be stored for extended periods of time in its soluble and injectable form in cold temperature, and "activated" at the time of injection to form a gel in situ at body temperature. Both the storage modulus (G') and the loss modulus (G") were also shown to increase as a function of time at 37° C. The change in tendon extracellular matrix solution moduli was depicted as a sigmoidal shaped increase, initiated approximately after 15 minutes, with a plateau that was reached after 20 minutes (FIG. 4b, right graph). 20 minutes corresponded well to the time it takes for the tendon extracellular matrix solution to completely form a gel in vitro, as observed macroscopically.

Scanning Electron Microscopy (SEM).

Scanning electron microscopy of specimens showed a distinct correlation between temperature and fiber definition. At lower temperatures (4 and 25° C.), collagen fibers were only partially developed, and individual fibers were aggregated by amorphous clumps, with less aggregation at ambient temperature than at 4° C. At 37° C., fibers became characterized as individual strands, which were well defined and often aligned as bundles with porosity conducive to fluid flow and gas exchange (FIG. 5). After injection of tendon extracellular matrix solution into Wistar rats and subsequent gelation into tendon hydrogel that formed a supportive scaffold structure, as detailed in Examples 1 and 3, the collagen fibers retained their linearity, and aggregates of fibers were similarly aligned with well-defined individual fibrils in which typical collagen 'D banded morphology' was evident at high magnification (FESEM image). Furthermore, these resulting supportive scaffold structures supported cell growth, and invasion of the scaffolds with cells increased over time, as was observed, when comparing in vivo samples one and two weeks following the administration of the tendon extracellular matrix solution. Cells supported by the collagen scaffold became aligned with collagen fibers (FIG. 6).

In Vivo—Gel Volume.

Wistar rats tolerated the tendon extracellular matrix solution injections well, and no adverse effects were observed. The initial prominent subcutaneous mass (FIG. 7) gradually decreased over the first postoperative hour as the tendon extracellular matrix gelated and conformed to the available subcutaneous space (FIG. 7). Explants of the tendon extracellular matrix hydrogel at 7, 14 and 28 days showed a gradual decrease in size and weight. It became difficult to distinguish gel from connective tissue that had grown into the gel at 4 weeks (FIG. 8). Tissue ingrowth and regeneration at the site of injection was seen, with no evidence of capsule formation that would have indicated that the body reacted to the gel as being foreign tissue. This further exemplifies the good biocompatibility seen with the gel in vivo (FIG. 9).

In Vivo—Histology.

The tendon extracellular matrix gels were consistently confined to the subcutaneous space beneath the panniculus carnosus, subcutaneous fat and underlying para-spinus muscles (FIG. 7). All gels remained as a coherent entity with no sign of capsule formation at any time point. After 4 weeks, ongoing degradation and regeneration caused the gel to merge with the surrounding tissue (FIGS. 9 C and D). Interestingly, the collagen bundles were highly regular and oriented in longitudinal fashion along the underlying muscular surface. The same pattern was found on SEM. Cellular infiltration was documented at 3, 7, 14, and 28 days. FIG. 10A illustrates CD 68+ macrophage infiltration of the gel from surrounding fat and muscle tissue at 3 days. FIG. 10B is a nuclear counterstain that stains all live cells in an adjacent section whereas 11C is an immune-histochemical stain of CD68+ macrophages. At the early time points, cell ingrowth was preferentially seen in the superficial parts of the gel, as depicted in FIG. 9. However CD68+ cells continued to populate the full thickness of the gel at all time points. At 14 days, histology displayed increasing numbers of spindle shaped elongated fibroblast cells, on its surface as well as centrally (FIGS. 9 A and B).

In Vitro—Histology.

Multipotent adipo-derived stem cells (ASCs) mixed with tendon-derived extracellular matrix solution proliferated on the surface and infiltrated the gel. Spindle shaped cells were observed both on the gel surface as well as within the gels, with a regular distribution throughout the gel. Live/dead staining and SYTO green staining on whole tissue mounts of gels confirmed that reseeded cells were homogenously distributed throughout the gel. The fraction of nonviable cells remained low, indicating that the tendon extracellular matrix hydrogel appears well suited for delivery of cells, such as multipotent adipoderived stem cells, to the area of tendon injury in order to speed up tendon tissue repair and regeneration (FIG. 11).

Utility of the Described Injectable Extracellular Matrix Solution that Gelates In Situ to a Tendon Hydrogel.

The described tendon-derived hydrogel offers the advantage that it can be readily delivered as injectable extracellular matrix solution through a direct injection into the area of the tendon or ligament injury.

Upon injection of the tendon-derived extracellular matrix solution, at a temperature (4-25° C.) where the solution is fully liquid, into an area of tendon or ligament injury and subsequent gelation at physiological body temperature (37° C.), the resulting tendon hydrogel forms a mesh of collagen fibers and collagen fiber bundles characterized by a highly regular linear pattern and orientation in longitudinal fashion along the underlying muscular surface. The regular pattern and longitudinal orientation is instrumental in rebuilding the injured tendon or ligament in a way that it regains the structural, biomechanical and functional characteristics of a normal, healthy tendon or ligament with its full range of motion and tensile strength.

Seeding of the tendon-derived extracellular matrix solution with rat adipoderived stem cells did not affect the biocompatibility of the resulting tendon hydrogel upon administration into rats, as evidenced by the lack of capsule formation. Capsule formation would have indicated that the body reacted to the extracellular matrix as being foreign tissue.

Example 2: Injectable Porcine Tendon Hydrogel as a Scaffold for In-Situ Guided Tissue Regeneration in the Musculoskeletal System 2.1 Experimental Procedures Tissue Decellularization and Material Processing for the Manufacture of Human Tendon Hydrogel.

Flexor tendons were harvested from fresh cadaveric forearms, as described in example 1. These tendons were meticulously debrided of remaining synovial material and muscle tissue. Flexor digitorum superficialis tendons were transected 2 cm proximal to the chiasma, while flexor digitorum profundus and flexor pollicis longus tendons were transected 1 cm proximal to the osteotendinous insertion. Harvested tendons were subsequently cut into 1 cm segments and treated with 0.1% ethylenediaminetetraacetic acid (EDTA) for 4 hours and then washed in 0.1% sodium dodecyl sulfate (SDS) in 0.1% EDTA for 24 hours at ambient temperature with constant agitation. Tendon was then rinsed in 1×PBS for 4 hours and stored at −80° C.

Tissue Decellularization and Material Processing for the Manufacture of Porcine Tendon Hydrogel.

Tendon was harvested from the dorsal and volar regions of fresh pig hindlimbs and meticulously debrided from remaining synovial material and muscle tissue. Harvested tendon was cut into 1 cm segments and treated with 0.2% ethylenediaminetetraacetic acid (EDTA) for 4 hours followed by 0.2% sodium dodecyl sulfate (SDS) in 0.2% EDTA for 24 hours at ambient temperature with constant agitation. Tendon was then rinsed in 1×PBS for 4 hours and stored at −80° C.

The frozen, decellularized tendons derived from human and porcine sources were lyophilized for 48 hours (Labconco, Kansas City, Mo., USA), and milled into a fine powder using a Wiley Mini Mill, filter size 80 (Thomas Scientific, Sedesboro, N.J., USA). The tendon powders were stored at 4° C. until use.

Confirmation of Decellularization.

To confirm decellularization of human as well as porcine tendon powders, cell visualization via routine H&E staining and SytoGreen 11 fluorescent staining was performed. In addition, DNeasy Assay was used to quantify the amount of nucleic acid present in decellularized samples. First, DNA was extracted from decellularized freeze-dried human as well as porcine tendon. Using the absorbance peak at 260 nm as a proxy, the concentration of dsDNA present in the extract was quantified using an ultraviolet spectrophotometer (Biophotometer 22331; Eppendorf, Hauppauge, N.Y., USA). The concentration of dsDNA present within samples was then extrapolated using a known extinction coefficient for the molecule.

Gel Formation from Extracellular Matrix Solution.

Based on previous optimization experiments, as described in example 1, human tendon powder was enzymatically digested by the addition of 1 mg ml$^{-1}$ pepsin in a 0.02M HCl solution to obtain a final concentration of 20 mg ml$^{-1}$ or 2%. The material was digested for 24 hours at ambient (room) temperature with constant stirring to ensure homogeneity. Analogously to the described method of digestion of human tendon powder, porcine tendon powder was digested by the addition of 0.1 mg ml$^{-1}$ pepsin in a 0.01M HCl solution. Final concentrations of the material were 10, 15, and 20 mg ml$^{-1}$ or 1, 1.5, and 2% respectively. The material was digested for up to 24 hours at ambient temperature with constant stirring. Microscopic observation of the resulting extracellular matrix solution demonstrated that optimal digestion of milled porcine tendon powder occurred at about 1 hour of stirring.

Prior to use, human and porcine tendon extracellular matrix solutions, respectively, were cooled on ice. Pepsin was denatured by the addition of 1M NaOH until the pH of the mixture reached 8.5. The pH was subsequently adjusted to 7.4 by the addition of 1M HCl. The salinity of the solution was also adjusted to physiologic levels by the addition of 10×PBS in a 1:10 fashion (1 ml 10×PBS per 10 ml gel).

Storage of Gel.

Human and porcine tendon extracellular matrix solutions, respectively, were stored at 4° C. following digestion until use. The extracellular matrix solutions were left acidified at pH 2 until the time of the experiment. At that point, solutions were alkalized to denature pepsin and then brought to physiologic pH as described above.

Mass Spectrometry.

Mass spectrometry (LTQ Orbitrap Velos, Thermo Scientific, Vancouver, Canada) was performed on milled decellularized porcine tendon prior to pepsin digestion. Analytic samples were prepared using a FASP (Wisniewski et al., 2009) protocol. A small amount of the tendon powder was solubilized in SDS, DTT and Tris-HCL, and digested overnight by trypsin. The resulting peptide fragments were then loaded onto a self-packed fused silica C18 analytical column with a Bruker Michrom Advance interface (Auburn, Calif., USA). A flow rate of 600 nL/min and a spray voltage of 1.7 kV were utilized. The mass spectrometer was set in data dependent acquisition mode and the 12 most intense precursor ions were detected. The data was converted to mzXML format and searched against the human uniprot-sprot database using Sequest on a Sorcerer platform. Scaffold 3 (Proteome Software, Portland, Oreg., USA) was used to analyze the data.

Rheology: Storage Modulus, Temperature Characteristics.

Rheological studies were performed with a TA Instruments ARG2 Rheometer. Extracellular matrix solution samples were dispensed (500 μl) onto two parallel steel plates (40 mm diameter) at a gap height of 100 μm, which allowed the solution to completely spread to the edge of the probe. Excess solution was gently wiped away. Using a barrier for containment, silicone oil was used to prevent evaporation of the sample. The storage modulus (G') and loss modulus (G") were measured for range of frequencies (0.1-10 rad s$^{-1}$) at 25° C. and 37° C. (frequency sweep). The samples were then subjected to increasing temperatures ranging from 25° C. up to 37° C. at a rate of 2° C. per minute with a frequency 1 rad s$^{-1}$ (temperature sweep). The temperature was then held at 37° C. for 30 minutes, until the hydrogel had formed, and the storage and loss moduli were measured (time sweep).

Live/Dead Assay of Human Adipo-Derived Stem Cells Reseeded on Human or Porcine Tendon Hydrogels.

Human adipo-derived stem cells (ASCs) were gently mixed with human and porcine tendon-derived extracellular matrix solutions, respectively, and incubated at 37° C. A Live/Dead assay (Promega, Madison, Wis., USA) was performed on the subsequently polymerized human and porcine hydrogels 7 days after seeding to assess the ratio of viable to nonviable cells. Cell-seeded tendon hydrogels were gently mixed with the staining agents and incubated per standard protocol.

Cell Proliferation of Reseeded ASCs.

Cell proliferation in human and porcine tendon hydrogels, respectively, was evaluated by the MTS colorimetric assay. Human adipo-derived stem cells (up to passage 4, Poietics PT-5006 cryopreserved adipoderived stem cells, Lonza, Walkersville, Md., USA) were cultured in fetal bovine serum (Gibco, Life Technologies, Grand Island, N.Y., USA) supplemented ADSC-BM medium (Lonza, Walkersville, Md., USA). ASCs were grown until 90% confluence at 37° C. in humidified tissue culture chamber with 5% $CO_2$ content. The tendon hydrogels were seeded with ASCs and cell proliferation was measured at 3, 5, 7, and 10 days thereafter. Tetrazolium dye (Cell Titer 96 Aqueous Nonradioactive Cell Proliferation Assay, Promega, Madison, Wis., USA) was directly added to wells in a 1:10 fashion, gently mixed, and allowed to incubate at 37° C. for 30 minutes. The contents of individual wells were transferred to microcentrifuge tubes and spun at 5000 g for 2 minutes to pellet hydrogel and cells. The supernatant was then collected and plated for reading. Proliferation was represented by absorbance values (optical density, O.D.) of the supernatant at 490 nm using an Epoch spectrophotometer (BioTek, Winooski, Vt., USA).

2.2 Tendon-Derived Porcine Hydrogel: Comparison to Tendon-Derived Human Hydrogel Manufacture of Human and Porcine Gel.

Human tendon was successfully decellularized, as described supra. The decellularization protocol for human tendon was unsuited to remove cells from porcine tendon and was, therefore, step-wise altered until decellularization in porcine tendon was achieved with 0.2% EDTA followed by 0.2% EDTA in 0.2% SDS, as confirmed by H&E staining (FIG. 12a) and SytoGreen 11 fluorescent staining (FIG. 12b). DNeasy Assay yielded a concentration of 132 ng dsDNA per mg decellularized tendon, a value similar to that obtained from decellularized human tendon (Pridgen et al., 2011).

ECM Gel Formation—Digestion Time and Concentration.

Human tendon hydrogel at a concentration of 20 mg/ml (2%) was successfully prepared based on methods and optimization experiments outlined in Example 1. Porcine tendon extracellular matrix solutions ranging from 10 mg/ml (1%) to 20 mg ml$^{-1}$ (2%) were evaluated, and the 1% porcine solution was chosen for rheological, biocompatibility, and proliferation studies, because of its superior handling properties, cellular proliferation profile, and structural integrity in comparison to other concentrations.

Details of Digestion.

Human tendon-derived extracellular matrix solution was digested for 24 hours with 1 mg/ml pepsin, whereas porcine tendon extracellular matrix solution was digested for only 1 hour with 0.1 mg/ml pepsin. The extent of digestion was assessed microscopically, as described in Example 1. FIG. 13 details human and porcine gel samples that have undergone over-, under-, and optimal digestion.

Storage of Porcine Tendon Extracellular Matrix Solutions.

The porcine tendon-derived extracellular matrix solutions gradually lost their ability to form gels over ensuing weeks unless the samples were stored at pH 2.2. At pH 2.2, liquefied porcine tendon extracellular matrix solutions can be stored for prolonged periods, with unchanged gelation properties following neutralization to pH 7.4.

Mass Spectrometry.

Proteome analysis of porcine tendon powder was performed following filter-aided sample preparation (FASP) and mass spectroscopy, which yielded 150 of the most abundant proteins in the sample. The 15 most abundant proteins are illustrated in FIG. 14. Collagen represented the most predominant protein family, constituting 32.3% of the total sample. Collagen 6A3 was the most abundant single protein in the sample (17.1% of the total content) followed by Collagen 6A2 (9.2%). A number of other extracellular matrix proteins were also found in the sample.

Rheology.

The rheological properties of 2% human and 1% porcine tendon-derived extracellular matrix solutions and their subsequently formed tendon hydrogels were determined using triplicates of the storage (G') and loss moduli (G"). Representative samples are shown in (FIG. 15). Frequency sweeps were performed to demonstrate the elastic and viscous tendencies of the samples at a range of angular frequencies as shown in FIGS. 15A and 15B. At 25° C., G' at 1 rad/s was found to be 177.9 and 137.9, while G" was 27.6 and 34.1 for human and porcine samples, respectively. At 37° C., G' at 1 rad/s was found to be 236.0 and 113.2, while G" was 22.5 and 12.4 for human and porcine samples, respectively.

To determine the effect of temperature on G' and G", a temperature sweep was performed (FIG. 15C). As the temperature increased from 25° C. to 37° C. at a rate of 2° C. per minute, the storage modulus for the human tendon extracellular matrix solutions increased from 180.6 to 208.3. Yet, the storage modulus for the porcine tendon extracellular matrix solutions decreased from 139.8 to 108.0. Once the temperature reached 37° C., the extracellular matrix solutions were monitored without further increases in temperature via a time sweep. In both human and porcine samples, the storage modulus (G') minimally increased, while the loss modulus (G") minimally decreased as a function of time, as depicted in FIG. 15D.

In Vitro—Live/Dead Staining and Cell Morphology.

Human adipo-derived stem cells were gently suspended within porcine and human tendon-derived extracellular matrix solutions, respectively, and proliferated within the subsequently formed hydrogels for 7 days at 37° C. For human and porcine samples alike, spindle shaped cells were observed (FIG. 16), displaying an even distribution throughout the solution. Over the course of 7 days, the fraction of nonviable cells remained low as assessed visually by the live/dead assay (FIG. 17).

Cellular Proliferation.

Human adipo-derived stem cells were seeded within human and porcine tendon-derived extracellular matrix solutions, respectively, and incubated at 37° C. where human and porcine tendon hydrogels, respectively, formed. At days 3, 5, 7, and 10 after seeding, there was no significant difference between the proliferation of cells within the human and porcine tendon hydrogel samples, respectively, as determined by tetrazolium dye assay (FIG. 18).

Utility of the Described Injectable Extracellular Matrix Solution Derived from Porcine Tendon Material.

An animal source for the tendon extracellular matrix is beneficial with respect to lower costs and higher availability in comparison to obtaining the connective tissue from a human cadaver. Also, the use of animal tissue might possibly raise less ethical concerns than the harvesting of tendon tissue from a human cadaver.

Since the connective tissue found in pig tendon is denser than that in human tendon, the decellularization process is more difficult for pig tendon than for human. However, once decellularization is achieved in pig tendon, the resulting powder requires then less time and amount of digesting enzyme to achieve full digestion, compared to human tendon.

Extracellular matrix solutions obtained from pig tendon proved to have a higher viscosity than extracellular matrix solutions obtained from human tendon and, therefore, a 1% extracellular matrix solution from pig tendon was found most useful to use with respect to ease of handling in liquid format.

Like extracellular matrix solution from human tendon, the extracellular matrix solution from pig tendon was liquid at temperatures below 25° C. (4-25° C.) and polymerized when the temperature was increased to physiological levels (37° C.). When extracellular matrix solution from pig tendon was seeded with human adipo-derived stem cells, standard cellular proliferation of the cells was observed without any significant difference between cellular proliferation in extracellular matrix solution from human versus pig tendon. This provides evidence that porcine tendon extracellular matrix can be seeded with human cells that would persist, in the polymerized form of the porcine tendon hydrogel, at the site of tendon or ligament injury of a mammalian subject and would sustain the growth of such cells. As such, the extracellular matrix solution from pig tendon holds the potential to be useful as an injectable composition for promoting the in-situ repair and regeneration of injured ligaments and tendons in a mammalian subject.

II. Method or In-Situ Repair and Regeneration of an Injured Tendon in a Mammalian Subject, Comprising Administering to Said Subject Suffering from an Injured Tendon a Therapeutically Effective Amount of a Composition into Said Subject's Area of Injured Tendon, Said Composition Comprising Decellularized Extracellular Matrix Derived from Tendon Connective Tissue, Said Composition being in Injectable Form Below 25 Degree Celsius and Forming Gel Upon Administration into Subject's Area of Injured Tendon

Example 3: Injectable Tendon Hydrogel Augments Tendon Healing in an Rat Achilles Tendon Injury Model 3.1 Experimental Procedures Tissue Decellularization and Material Processing to Obtain Decellularized and Lyophilized Extracellular Matrix Material for the Subsequent Preparation of a Tendon (Hydro)Gel.

Human flexor digitorum profundus (FDP), flexor digitorum superficialis (FDS) and flexor pollicis longus (FPL) tendons were harvested from fresh-frozen human cadaveric forearms and processed as described in Example 1.

Extracellular ECM Gel Formation.

The extracellular matrix material was enzymatically digested by adding a 1 mg/ml solution of pepsin (Sigma, St Louis, Mo.) in 0.02 M HCl and sterile water such that the final concentration of material was 20 mg/ml, and pH was 2.2. The material was digested for 24 hours at room temperature with constant stirring. While the resulting liquid cooled on ice, the pH was first raised to 8 using NaOH to deactivate the pepsin, then lowered to 7.4. Salt concentration was adjusted using 10×PBS to achieve an isotonic solution.

Surgical Procedure and Treatment.

Acute, bilateral Achilles tendon injuries were produced in 36 Wistar rats (mean weight 350 g) by surgical removal of part of the Achilles tendon substance (about half of the tendon substance was removed). All animals were kept anesthetized with isofluorane in a prone position. A slightly curved 1 cm incision was made lateral to the Achilles tendon to create a skin flap, ensuring that the Achilles tendon defect would not be created immediately under the skin wound. Great care was taken not to harm the sural nerve or large vessels in the dissection. Two surgical blades (size 15, Fisher Scientific) bonded with cyanoacrylate were used to make parallel incisions in the tendon 0.5 mm apart and 5 mm long, spanning from the TBI at the calcaneus to mid-tendon (FIG. 19). This was performed under magnification using an operating microscope (Zeiss Opthalmic Surgical/Operative Microscope OPMI 6-SDFC, West Germany). Microscissors were used to remove the scored sections, such that a full-thickness defect was created mid-substance (within the middle of the tendon longitudinally). A pair-matched design was employed to compare the gel effect on one leg to a saline control on the other leg.

The defect that resulted from the partial Achilles tendon removal on the rats' one side was filled with 0.05 mL of injectable, solubilized extracellular matrix (2%), which was solubilized as described above and which gelated in situ at the site of injection as described in Example 1; the defect on the rats' corresponding other leg was filled with 0.05 mL of PBS (FIG. 19. The wound was closed with 4-0 resorbable Vicryl stitches. Preoperatively, the rats had received an intravenous injection of 0.05 mg/kg buprenorphine (Buprenex) for pain management, and an intravenous injection of 20 mg/kg enrofloxacin (Baytril) as antibiotic prophylaxis. All animals, including the control animals, were given the same per-operative treatment and medication.

At 2, 4 and 8 weeks following the procedure of removing tendon and filling with extracellular matrix or saline, 12 rats were sacrificed per time point and the Achilles tendons on both legs of the rats were harvested. The time points were determined based on the results of a pilot study which had been conducted with 1 week, 2 weeks, and 4 weeks time points. The 1-week time point was eliminated to minimize any effects of variation in the surgical procedure, and the 8 week time point was added to observe a longer healing period. The rats were sacrificed via carbon dioxide inhalation and subsequent lung puncture. From the 12 rats per time point, ten at each time point were used for biomechanical testing, while the other two were used for histology.

Biomechanical Testing.

Biomechanical testing was carried out with the Mini Bionix testing system (MTS Systems, Eden Prairie, Minn., USA), using a 50-lb load cell. Tendons were harvested still attached to the rat foot. Muscle was completely removed from the tendon such that the tendon-muscle insertions (proximal extent of the tendon, where it inserts into the gastrocnemius muscle) were exposed. A custom rig was used to secure the foot while the tendon-muscle insertions were clamped between sandpaper and cyanoacrylate.

Orthogonal photographs together with a known scale (digital caliper) were obtained using a digital camera (8.2 megapixel Canon EOS 30D, Tokyo, Japan) at a fixed distance to measure two dimensions of the tendon. The cross-sectional area was calculated using an elliptical assumption (ImageJ software, NIH) and used to calculate the ultimate tensile stress (UTS). Tendons were stretched at a rate of 0.5 mm/sec until failure. The ultimate failure load (UFL) was recorded; UTS was computed from UFL and cross-sectional area data; stiffness was determined from force/displacement curves. These curves were obtained by computer registering the MTS forces. The treatment groups were compared using a paired Student's t-Test.

Histological Analysis.

Formalin-fixed, paraffin-embedded sections (6 μm) were stained with hematoxylin and eosin to assess tendon morphology. Adjacent slides were stained with Picro-sirius Red solution to assess collagen I and collagen III content. All images were taken with a Leica DM5000B fluorescent microscope, with a polarizing filter for Picro-sirius Red stains.

3.2 Comparative Results for In-Vivo Guided Tendon Regeneration Using Injectable Tendon-Derived Extracellular Matrix Solution, that Gelates In Situ to Tendon Hydrogel, Versus Saline Control Biomechanical Properties.

One animal from each time point was excluded because of tendons slipping out of the clamp during testing and losing their tendon-muscle insertions. At 2 weeks, the majority of ruptures occurred in the mid substance of the tendon. At 4 and 8 weeks, ruptures were more common at the tendon-bone insertion.

There was no significant difference in UFL ($p=0.151$), UTS ($p=0.424$), and stiffness ($p=0.760$) between the gel and PBS treatments at the early 2-week time point. However at 4 weeks, tendons treated with gel had UFLs that were 28% stronger on average than those treated with PBS ($74.8\pm11.6$ N for gel-treated vs. $58.4\pm14.2$ N treated with PBS, $p=0.016$) (FIG. 20); at this time point, the tendons that had been treated with tendon hydrogel had already reached near-native strength. There remained no significant difference in UTS ($p=0.634$) and stiffness ($p=0.082$). By 8 weeks there was no longer a significant difference in UFL ($p=0.156$) between treatments, since near-native strength had already been achieved at the 4-weeks timepoint. There remained no significant difference in UTS ($p=0.385$) and stiffness ($p=0.748$).

Histological Results.

Cross-sections of both treatment groups (gel treatment vs. treatment with PBS) showed similar injury morphologies at 2 and 4 weeks, where the wound defect was clearly visible between tendon portions. By 8 weeks, the wound space was indiscernible from healing tendon tissue. No capsule formation was observed which would have indicated that the body reacted to the gel as being foreign tissue; rather, the gel might have acted to facilitate infiltration by the host cells. At 2 weeks, Picro-sirius Red staining revealed a very strong presence of collagen I in the wound trough of tendons treated with gel that is absent in those treated with saline. By 4 weeks, a noticeable difference in the collagen content of the injury troughs could be observed suggesting that the gel might have promoted early collagen I formation within the trough. The collagen I at this time point is aligned with the healing collagen III and does not match the morphology of the digested, unaligned collagen I seen at 2 weeks. At 8 weeks, the collagen content of the healing areas was indistinguishable in both, the gel-treated and the PBS-treated, groups.

Utility of the Described Injectable Tendon-Derived Extracellular Matrix Solution that Gelates In Situ to Tendon Hydrogel.

Comparing the Achilles tendon repair and regeneration process during the first eight weeks following acute, bilateral Achilles tendon injuries (by partial removal of the Achilles tendon) in a rat model illustrates that the application of tendon-derived extracellular matrix solution to the site of injury supported and accelerated the tendon healing process, as measured by superior biomechanical function at 4 weeks after injury in comparison to the application of saline, as control. Tendon-derived extracellular matrix solution is liquid at or below room temperature (4-25 degree Celsius), but, upon administration into a mammalian subject, such as a rat, at the site of tendon injury forms right there, in situ, at physiological temperature, a tendon hydrogel. The Achilles tendons that were treated with the hydrogel ('gel-treated') were significantly stronger after four weeks than the Achilles tendons that were filled with saline only ('saline-treated', see FIG. 20). An ultimate failure load (strength) of 74.8N of the gel-treated tendons compared to 58.4N was seen at 4 weeks following the administration of the tendon-derived extracellular matrix hydrogel. This corresponded to an about 28% higher strength in the gel-treated group compared to the saline-treated group. In fact, at that 4-weeks time point, the gel-treated tendons were found to be as strong and possessing the same stiffness as native tendons according to previously assessed values for native tendons, namely $74.8\pm11.6$N gel-treated tendon versus $75.7\pm18.5$ native tendon for strength and $17.9\pm3.5$ gel-treated tendon versus $17.9\pm5.5$ native tendon for stiffness).

Furthermore, a histological evaluation of the gel-treated versus saline-treated tendons revealed cellular ingrowth in the gel-treated tendon which was not observable in the saline-treated controls: at the same 4-week time point, where gel-treated tendons were found about 28% stronger than saline-treated controls, it was observed that early collagen I had formed in the gel-treated tendons, whereby such early collagen I was aligned with healing collagen III fibers. Picro-sirius Red staining of the gel-treated and saline-treated tendons at the 4-week time point showed a considerably higher collagen I:collagen III ratio in the gel-treated tendons compared to saline-treated controls (see FIG. 21).

While collagen III fibers typically occur during the second healing phase of collagen proliferation, as described earlier, the formation of early collagen I is not typical and was primarily observed in gel-treated tendons. The formation of early collagen I and its alignment with healing collagen III, therefore, indicates that the presence of the tendon hydrogel induced the infiltration of host cells into the site of tendon injury and, thus, exerted biological and chemical cues onto the cellular environment. The fact that collagen I fibers are more robust then the thinner collagen III fibers might explain the superior strength of gel-treated tendons at the 4-week time point.

Ancillary investigations of the described tendon hydrogels that were detailed in Example 1 had revealed that the hydrogel was well tolerated by a mammalian subject such as a rat, that it did not form a capsule and, of particular noteworthiness, that it gradually degraded over a period of about four weeks. This lends very reasonable support to the described observation in the acute, bilateral Achilles tendon injury rat model, where—after four weeks—gel-treated tendons proved to be 28% stronger than controls and infiltrated with supporting host cells which accelerated the healing process in comparison to saline-treated controls.

Since the gel gradually degrades over a period of about four weeks, its full benefits should occur early, likely peak at the 4-week time point, as was observed in the described studies, and decrease over the remaining healing period up to 8 weeks. At the 8-week time point, the tendons of both the gel-treated and the saline-treated groups were found to be primarily composed of the robust collagen I and had no further differences in strength.

In the clinical setting, administration of such an injectable extracellular matrix solution that gelates in situ could improve tending healing in a mammalian subject by accelerating the healing process, providing increased strength to the healing tendon and, thus, allowing for more rapid mobilization and weight-bearing of the injured tendon. This applies to cases of extensive, traumatic tendon injuries which require surgery; here, the administration of such an injectable extracellular matrix solution that gelates in situ following the surgery would support and accelerate healing. Furthermore, the administration of injectable extracellular matrix solution that gelates in situ would support and accelerate healing in cases of microscopic tendon injuries that are characterized by tears, but not full ruptures of tendon and usually don't require surgical intervention. The mere administration of injectable extracellular matrix solution that gelates in situ might be sufficient to regenerate the microscopically injured tendon to its native strength.

This accelerated rebuilding and healing process can be furthermore supported and enhanced by adding (i) external cells such as stem cells, progenitor cells and fibroblasts, (ii) growth factors such as insulin-like growth factor-I (IGF-I), transforming growth factor beta (TGFbeta), vascular endothelial growth factor (VEGF), platelet-derived growth factor (PDGF), and basic fibroblast growth factor (bFGF) and/or (iii) platelet-rich plasma to the tendon-derived extracellular matrix solution prior to injection into the area of ligament or tendon injury. As detailed in example 1, seeding of the tendon-derived extracellular matrix solution with rat adipoderived stem cells did not affect the biocompatibility of the resulting tendon hydrogel upon administration into rats, as evidenced by the lack of capsule formation.

III. Method or In-Situ Repair and Regeneration of an Injured Ligament in a Mammalian Subject, Comprising Administering to Said Subject Suffering from an Injured Ligament a Therapeutically Effective Amount of a Composition into Said Subject's Area of Injured Ligament, Said Composition Comprising Decellularized Extracellular Matrix Derived from Tendon Connective Tissue, Said Composition being in Injectable Form Below 25 Degree Celsius and Forming a Gel Upon Administration into Subject's Area of Injured Ligament Example 4: Injectable Tendon Hydrogel to Treat Ligament Injuries Tendon overuse in both professional and recreational settings gradually alters the biomechanical properties of both tendons and ligaments. Both of these tissues have structural properties and a tissue composition that is very similar. Structural changes seen at injuries typically first present as microscopic tears that, after a period of accumulation, may lead to full-thickness injuries. Common ligament injuries include the ligaments of the wrist, base of thumb, elbow and shoulder. The tendon hydrogel contains the appropriate extracellular matrices (ECMs) of ligaments and therefore, the healing of a ligamentous injury may also be augmented by the introduction of a tendon-derived hydrogel into the injury site.

Example 5: Injectable Human Tendon Nanogel Enhances Cellular Integration into Nano-Matrix Scaffolds High-frequency ultrasound was applied to human tendon extracellular matrix solution to produce single collagen fibers with a fibrillar diameter in the nanometer range. The matrix solution was then seeded prior to gelation, as described earlier. The application of ultrasound was found to enhance the formation of a collagen network into nanoscaled fibers (nano-matrix scaffold, see FIG. 22) and resulted in improved reseeding with retained hydrogel properties. A

TABLE 3

Comparison of biomechanical properties of tendon-derived hydrogel-treated (gel-treated) versus saline-treated tendons

| Group | Treatment | Number of limbs used for biomechanical testing and histology, respectively | Ultimate Failure Load (N) | Ultimate Tensile Stress (N/mm$^2$) | Stiffness (N/mm) | Failure mode |
|---|---|---|---|---|---|---|
| 1 | 2 weeks Gel | 10 strength 2 histology | 45.2 ± 8.6 (ns) | 1.6 ± 0.6 (ns) | 11.4 ± 3.7 (ns) | 1 TBI 8 tendon 0 bone |
|   | 2 weeks Saline | 10 strength 2 histology | 39.8 ± 6.3 (ns) | 1.4 ± 0.2 (ns) | 10.9 ± 2.7 (ns) | 2 TBI 7 tendon 0 bone |
| 2 | 4 weeks Gel | 10 strength 2 histology | 74.8 ± 11.6 (*) | 3.0 ± 0.7 (ns) | 17.9 ± 3.5 (ns) | 5 TBI 4 tendon 0 bone |
|   | 4 weeks Saline | 10 strength 2 histology | 58.4 ± 14.2 (*) | 2.8 ± 1.0 (ns) | 14.7 ± 3.9 (ns) | 7 TBI 2 tendon 0 bone |

TBI = tendon bone insertion
ns = non significant
(*) = p < 0.05 tendon nanogel represents, therefore, an efficacious cell-hydrogel delivery system with enhanced cellular integration and an improved collagen network for cellular delivery.

Materials and methods. A 450 sonifier cell disruptor was used to apply the high-frequency ultrasound with settings of 2×/10×/20×/40×/60× at 65 watts employing intermittent-pulser mode with 2-seconds cycles. A VP-SEM 3400N-Zeiss Sigma scanning electron microscope was used to obtain optical microscope pictures of gel samples at 40× magnification following 2 cycles, 10 cycles, 20 cycles, 40 cycles and 60 cycles, in comparison to control (no ultrasound), see FIG. 23. All samples had been fixed in glutaraldehyde. The average fiber length was obtained by projection following manual counting 100 individual segments of fiber.

Cell proliferation and viability were assessed by Live cell assays at one week following seeding. The highest cell proliferation rate was observed with 20× (20 cycles of) ultrasonication, as illustrated in FIG. 24.

Nanogel polymer size, porosity and cell-to-matrix interactions were characterized with scanning electron and laser scanning confocal microscopy (Leica SP8, Leica Microsystems CMS). Fiber measurements were obtained using ImageJ Software, bandpass filter, 200 pores.

Increased cell proliferation was seen at day 7 in the nanogel compared to control (p=0.0002) and Live/Dead staining confirmed viability (FIG. 25). Scanning Electron Microscope demonstrated the creation of a porous network with an average pore diameter of 1.38±0.73 μm and an average collagen fibrillar diameter of 0.17±0.06 confirming nano-hydrogel properties (FIGS. 26, 27). Scanning electron and confocal microscopy demonstrated the presence of cell clusters at day 1 post-reseeding in the nanogel with preserved hydrogel properties (FIG. 28). For confocal microscopy (40× water immersion objective, zoom factors 1-2.5×), Hoechst 3342 fluorescent stain and alexa fluor 488-phalloidin were used with a 405 nm excitation wave and 475/515 nm collected emission.

In vivo behaviour was assessed for host cell repopulation and remodeling in a Sprague Dawley rat model (n=4) following dorsal injection of 1 mL of extracellular matrix solution that was non-seeded or seeded with rats luciferase-firefly transfected fibroblasts and was ultrasonicated or not ultrasonicated. See FIG. 29A with a: non-reseeded, not ultrasonicated; b: reseeded, not ultrasonicated; c: non-reseeded, ultrasonicated; d: reseeded, ultrasonicated.

It is notable that upon injection the nanogel formed at the site of injection with little to no diffusion into subcutaneous layers (FIG. 29B). FIG. 29C shows bioluminescence results. No statistically significant difference between the ultrasonicated (nanosized hydroge, 'Nanogel') and not ultrasonicated ('Hydrogel') tendon material was observed (FIG. 30). H&E staining on frozen sections from the same in-vivo samples shows the presence of a vascular network in the reseeded, ultrasonicated 'Nanogel' samples (FIG. 31, B2 and B4). Anti-Firefly Luciferase immunohistochemical staining of subcutaneous tissue from rat dorsum that had been injected with rats luciferase transfected fibroblasts, as described in FIG. 29, showed that few fibroblasts had remained after 7 days following injection (FIG. 31).

Although the foregoing invention and its embodiments have been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. Accordingly, the preceding merely illustrates the principles of the invention.

It will be appreciated that those skilled in the art will be able to devise various arrangements which, although not explicitly described or shown herein, embody the principles of the invention and are included within its spirit and scope.

10. REFERENCES

Adair-Kirk T L & Senior R M (2008). Fragments of extracellular matrix as mediators of inflammation. The international journal of biochemistry & cell biology. 40(6-7):1101-10.

Andersson T et al. (2012). Growth hormone does not stimulate early healing in rat tendons. International journal of sports medicine 33(3):240-3.

Archambault J M et al. (2007). Rat supraspinatus tendon expresses cartilage markers with overuse. J Orthop Res. 25(5):617-24.

Arya S & Kulig K (2010). Tendinopathy alters mechanical and material properties of the Achilles tendon. J Appl Physiol. 108(3):670-5.

Beck J et al. (2012). The biomechanical and histologic effects of platelet-rich plasma on rat rotator cuff repairs. Am J Sports Med. 40(9):2037-44.

Bohak Z (1969). Purification and characterization of chicken pepsinogen and chicken pepsin. The Journal of biological chemistry. 244(17):4638-48.

Brennan E P et al (2006). Antibacterial activity within degradation products of biological scaffolds composed of extracellular matrix. Tissue Eng. 2006; 12(10):2949-55.

Chong A K et al. (2007). Bone marrow-derived mesenchymal stem cells influence early tendon healing in a rabbit achilles tendon model. J Bone Joint Surg Am. 89(1):74-81.

Daamen W F et al (2003). Preparation and evaluation of molecularly-defined collagen-elastin glycosaminoglycan scaffolds for tissue engineering. Biomaterials 24(22):4001-9.

Davis G E et al (2000). Regulation of tissue injury responses by the exposure of matricryptic sites within extracellular matrix molecules. The American journal of pathology. 156(5):1489-98. Epub 2000 May 4.

DeQuach J A et al (2011). Decellularized porcine brain matrix for cell culture and tissue engineering scaffolds. Tissue Eng Part A 17(21-22):2583-92.

DeQuach J A et al (2012). Injectable skeletal muscle matrix hydrogel promotes neovascularization and muscle cell infiltration in a hindlimb ischemia model. European cells & materials 23:400-12; discussion 12.

Freytes D O et al (2008). Preparation and rheological characterization of a gel form of the porcine urinary bladder matrix. Biomaterials 29(11):1630-7.

Garg T et al. (2012). Scaffold: a novel carrier for cell and drug delivery. Critical reviews in therapeutic drug carrier systems 29(1):1-63.

Gimbel J A et al. (2004). Supraspinatus tendon organizational and mechanical properties in a chronic rotator cuff tear animal model. J Biomech. 37(5):739-49.

Gimble J M et al (2007). Adipose-derived stem cells for regenerative medicine. Circ Res. 100(9):1249-60.

Hall M P et al. (2009). Platelet-rich Plasma: Current Concepts and Application in Sports Medicine. J Am Acad Orthop Surg 17(10):602-608.

Hamada Y et al. (2012). The preparation of PLLA/calcium phosphate hybrid composite and its evaluation of biocompatibility. Dental materials journal 31(6):1087-96.

Huss F R et al. (2010. Use of macroporous gelatine spheres as a biodegradable scaffold for guided tissue regeneration of healthy dermis in humans: an in vivo study. J Plast Reconstr Aesthet Surg. 63(5):848-57.

Johnson T D et al (2011). Tailoring material properties of a nanofibrous extracellular matrix derived hydrogel. Nanotechnology 22(49):494015.

Joubert L-M (2009). Visualization of Hydrogels with Variable-Pressure SEM. Microsc Microanal. 15(Suppl. 2):1308.

Kampa R J & Connell D A (2010). Treatment of tendinopathy: is there a role for autologous whole blood and platelet rich plasma injection? International journal of clinical practice 64(13):1813-23.

Kannus, P (2000). Structure of the tendon connective tissue. *Scand J Med Sci Sports* 10:312-320.

Kannus P & Natri A (2007). Etiology and pathophysiology of tendon ruptures in sports. Scandinavian Journal of Medicine & Science in Sports 7:107-112.

Kenne L et al. (2013). Modification and cross-linking parameters in hyaluronic acid hydrogels definitions and analytical methods. Carbohydrate polymers 91(1):410-8.

Khan K M et al. (1999). Histopathology of common tendinopathies. Update and implications for clinical management. Sports Med. 27(6):393-408.

Kim J K et al. (2007). Preparation and properties of collagen/modified hyaluronic acid hydrogel for biomedical application. Journal of nanoscience and nanotechnology 7(11):3852-6.

Kurtz C A (1999). Insulin-like growth factor I accelerates functional recovery from Achilles tendon injury in a rat model. Am J Sports Med. 27(3):363-9.

Lin T W et al. (2004). Biomechanics of tendon injury and repair. Journal of Biomechanics 37 (6), p. 865-877.

Longo U G et al. (2008). Histopathology of the supraspinatus tendon in rotator cuff tears. Am J Sports Med. 36(3):533-8.

Longo U G et al. (2011). Tissue engineered biological augmentation for tendon healing: a systematic review. British medical bulletin 98:31-59.

Lu F et al. (2008). Improved viability of random pattern skin flaps through the use of adipose derived stem cells. Plast Reconstr Surg. 121(1):50-8. Epub 2008 Jan. 8.

Martinello T et al. (2012). Successful recellularization of human tendon scaffolds using adipose derived mesenchymal stem cells and collagen gel. Journal of tissue engineering and regenerative medicine. epub Jun. 19, 2012.

Meyers S A et al (1989). Effect of hyaluronic acid/chondroitin sulfate on healing of full-thickness tendon lacerations in rabbits. J Orthop Res. 7(5):683-9.

Mott J D & Werb Z (2004). Regulation of matrix biology by matrix metalloproteinases. Current opinion in cell biology. 16(5):558-64.

Nakaji-Hirabayashi T et al (2012). Improvement of neural stem cell survival in collagen hydrogels by incorporating laminin-derived cell adhesive polypeptides. Bioconjugate chemistry 23 (2):212-21.

Neviaser A et al. (2012). Basic mechanisms of tendon fatigue damage. J Shoulder Elbow Surg. 21(2):158-63.

Ngo M et al. (2001). Differential expression of transforming growth factor-beta receptors in a rabbit zone II flexor tendon wound healing model. Plast Reconstr Surg. 108 (5):1260-7.

Noth U et al (2005). Anterior cruciate ligament constructs fabricated from human mesenchymal stem cells in a collagen type I hydrogel. Cytotherapy 7(5):447-55.

Okamoto N (2010). Treating Achilles tendon rupture in rats with bone-marrow-cell transplantation therapy. J Bone Joint Surg Am. 92(17):2776-84.

Peng K T et al. (2010). Treatment of osteomyelitis with teicoplanin-encapsulated biodegradable thermosensitive hydrogel nanoparticles. Biomaterials 31(19):5227-36.

Pittenger M F et al (1999). Multilineage potential of adult human mesenchymal stem cells. Science 284(5411):143-7. Epub 1999 Apr. 2.

Pridgen B C et al (2011). Flexor Tendon Tissue Engineering: Acellularization of Human Flexor Tendons With Preservation of Biomechanical Properties and Biocompatibility. Tissue Eng Part C Methods. 17(8):810-28.

Sato D et al. (2012). Effect of platelet-rich plasma with fibrin matrix on healing of intrasynovial flexor tendons. J Hand Surg Am. 37(7):1356-63.

Seif-Naraghi S B et al (2010). Design and characterization of an injectable pericardial matrix gel: a potentially autologous scaffold for cardiac tissue engineering. Tissue Eng Part A 16(6):2017-

Seif-Naraghi S B et al. (2012). Injectable extracellular matrix derived hydrogel provides a platform for enhanced retention and delivery of a heparin-binding growth factor. Acta biomaterialia. 8(10):3695-703.

Sharma P & Maffulli N (2005). Tendon injury and tendinopathy: healing and repair. *J Bone Joint Surg Am* 87:187-202.

Sharma P & Maffulli N (2006). Biology of tendon injury: healing, modeling and remodeling. J Musculoskelet Neuronal Interact 6(2):181-190.

Singelyn J M et al (2009). Naturally derived myocardial matrix as an injectable scaffold for cardiac tissue engineering. Biomaterials 30(29):5409-16.

Singelyn J M et al (2012). Catheter-deliverable hydrogel derived from decellularized ventricular extracellular matrix increases endogenous cardiomyocytes and preserves cardiac function post myocardial infarction. J Am Coll Cardiol. 59(8):751-63.

Stabenfeldt S E & LaPlaca M C (2011). Variations in rigidity and ligand density influence neuronal response in methylcellulose-laminin hydrogels. Acta biomaterialia 7(12): 4102-8.

Suri S & Schmidt C E (2010). Cell-laden hydrogel constructs of hyaluronic acid, collagen, and laminin for neural tissue engineering. Tissue Eng Part A 16(5):1703-16.

Tapp H et al. (2009). Adipose-derived stem cells: characterization and current application in orthopaedic tissue repair. Exp Biol Med 234(1):1-9. Epub 2008 Dec. 26.

Tobita M et al (2008). Periodontal tissue regeneration with adipose-derived stem cells. Tissue Eng Part A 14(6):945-53.

Uysal C A et al (2012). Adipose-derived stem cells enhance primary tendon repair: Biomechanical and immunohistochemical evaluation. J Plast Reconstr Aesthet Surg. 65(12):1712-9.

Valentin J E et al (2009). Macrophage participation in the degradation and remodeling of extracellular matrix scaffolds. Tissue Eng Part A. 15(7):1687-94.

Virchenko O & Aspenberg P (2006). How can one platelet injection after tendon injury lead to a stronger tendon after 4 weeks? Interplay between early regeneration and mechanical stimulation. Acta orthopaedica 77(5):806-12.

Wisniewski J R et al (2009). Universal sample preparation method for proteome analysis. Nature methods. 6(5):359-62. Epub 2009 Apr. 21.

Wolf M T et al (2012). A hydrogel derived from decellularized dermal extracellular matrix. Biomaterials 33(29): 7028-38.

Yan X M et al (2012). Improved synthesis of hyaluronic acid hydrogel and its effect on tissue augmentation. Journal of biomaterials applications 27(2):179-86.

Young R G et al. (1998). Use of mesenchymal stem cells in a collagen matrix for Achilles tendon repair. J Orthop Res. 16(4):406-13.

Zhang X et al. (2012). Structural study and preliminary biological evaluation on the collagen hydrogel cross-linked by gamma-irradiation. J Biomed Mater Res A. 100(11):2960-9.

Zuk P A et al (2001). Multilineage cells from human adipose tissue: implications for cell-based therapies. Tissue Eng. 7(2):211-28. Epub 2001 Apr. 17.

What is claimed is:

1. A composition for in-situ repair and regeneration of an injured ligament or tendon not involving bone formation in a mammalian subject, comprising decellularized extracellular matrix that was derived from tendon connective tissue by enzymatic digestion at ambient temperature, said composition being in injectable form below 25 degree Celsius and forming a gel upon administration into said subject's area of injured ligament or tendon achieving in-situ repair and regeneration of said injured ligament or tendon not involving bone formation by creating in situ a support structure which facilitates infiltration of said subject's own fibroblasts and tenocytes into said support structure.

2. The composition in accordance to claim 1 comprising tendon connective tissue that was obtained from an allogeneic source.

3. The composition in accordance to claim 2 comprising tendon connective tissue that was obtained from a human.

4. The composition in accordance to claim 1, further comprising cells selected from the group consisting of stem cells, progenitor cells and fibroblasts.

5. The composition in accordance to claim 1, further comprising a therapeutic agent.

6. The composition in accordance to claim 4, further comprising a therapeutic agent.

7. The composition in accordance to claim 5, wherein said therapeutic agent is selected from the group consisting of growth factors, analgesics, antibiotics and platelet-rich plasma.

8. The composition in accordance to claim 6, wherein said therapeutic agent is selected from the group consisting of growth factors, analgesics, antibiotics and platelet-rich plasma.

9. The composition in accordance to claim 1 prepared for one-time administration.

10. The composition in accordance to claim 1 prepared for repeat administration.

11. The composition in accordance to claim 1 for use in in-situ repair of Achilles tendon, rotator cuff, patella tendon, common flexor tendon or common extensor tendon.

12. The composition in accordance to any of claim 1, 4, 5 or 6, wherein the composition is an injectable decellularized extracellular matrix derived from human tendon connective tissue.

13. The composition in accordance to claim 1, comprising decellularized extracellular matrix that was derived from tendon connective tissue and, furthermore, subjected to high frequency ultrasonication, and forming a gel upon administration into said subject's area of injured ligament or tendon, said gel comprising nanoscaled collagen fibers with an average diameter of 170 nm.

14. A method of producing a composition
    for in-situ repair and regeneration of an injured ligament or tendon not involving bone formation in a mammalian subject comprising decellularized tendon extracellular matrix that was derived from tendon connective tissue by enzymatic digestion at ambient temperature,
    said method comprising:
    (a) without termal denaturation processing tendon connective tissue from a donor to obtain decellularized tendon extracellular matrix; and
    (b) milling, powderizing and enzymatically treating said tendon extracellular matrix at ambient temperature.

15. The method in accordance to claim 14, wherein said decellularized tendon extracellular matrix is derived from an allogeneic source.

16. The method in accordance to claim 15, wherein said allogeneic source is human.

17. The method in accordance to claim 14, wherein said decellularized tendon extracellular matrix is, furthermore, subjected to high frequency ultrasonication.

* * * * *